US009962449B2

(12) United States Patent
Payne et al.

(10) Patent No.: US 9,962,449 B2
(45) Date of Patent: May 8, 2018

(54) MULTILIGAND AGENT FOR DRUG DELIVERY

(71) Applicant: Arcturus Therapeutics, Inc., San Diego, CA (US)

(72) Inventors: Joseph E. Payne, San Diego, CA (US); Padmanabh Chivukula, San Diego, CA (US); Steven P. Tanis, Carlsbad, CA (US)

(73) Assignee: Arcturus Therapeutics, Inc., San Diego, CA (US)

( * ) Notice: Subject to any disclaimer, the term of this patent is extended or adjusted under 35 U.S.C. 154(b) by 0 days. days.

(21) Appl. No.: 15/224,474

(22) Filed: Jul. 29, 2016

(65) Prior Publication Data

US 2017/0028074 A1    Feb. 2, 2017

Related U.S. Application Data

(60) Provisional application No. 62/199,577, filed on Jul. 31, 2015.

(51) Int. Cl.
| *A61K 31/713* | (2006.01) |
| *C12N 15/113* | (2010.01) |
| *A61K 47/48* | (2006.01) |
| *A61K 9/00* | (2006.01) |

(52) U.S. Cl.
CPC ...... *A61K 47/48123* (2013.01); *A61K 9/0019* (2013.01); *A61K 31/713* (2013.01); *A61K 47/48092* (2013.01); *C12N 15/113* (2013.01); *C12N 2310/14* (2013.01); *C12N 2310/3515* (2013.01); *C12N 2320/32* (2013.01)

(58) Field of Classification Search
CPC ........ A61K 47/48123; A61K 47/48092; A61K 9/0019; A61K 31/713; C12N 15/113; C12N 2310/14; C12N 2310/3515; C12N 2320/32
See application file for complete search history.

(56) References Cited

U.S. PATENT DOCUMENTS

| 8,158,601 | B2 | 4/2012 | Chen et al. |
| 8,450,467 | B2 | 5/2013 | Manoharan et al. |
| 8,598,139 | B2 | 12/2013 | Fitzgerald et al. |
| 2008/0108801 | A1 | 5/2008 | Manoharan et al. |
| 2014/0315835 | A1 | 10/2014 | Rajeev et al. |

FOREIGN PATENT DOCUMENTS

WO    WO 2015/074085 A1    5/2015

OTHER PUBLICATIONS

Zen et al.; "Synthetic Reactions of Aliphatc Nitro-Compounds III, The Synthesis and Configurational Analysis of 2-Hydroxymethyl-2-aminocyclohexanediol"; Bulletin of the Chemical Society of Japan; vol. 42; Jun. 1969; p. 1761-1762.
Wang et al., Alternative Copolymerization of a Conjugated Segment and a Flexible Segment and Fabrication of a Fluorescent Sensing Film for HCl in the Vapor Phase; Chemistry an Asian Journal; vol. 8; 2013; p. 101-107.
International Patent Application No. PCT/US2016/044921; Int'l Preliminary Report on Patentability; dated Feb. 15, 2018; 8 pages.
Lee et al.; "Synthesis and Evaluation of Eight- and Four-Membered Iminosugar Analogues as Inhibitors of Testicular Ceramide-Specific Glucosyltransfrase, Testicular B-Glucosidase 2, and other Glycosidases"; The Journal of Organic Chemistry; vol. 77; 2012; p. 3082-3098.
Lohse et al.; "Synthesis of 3-substituted isofagomine analogues using an unusual syn hydrogenation reaction"; J. Chem. Soc., Perkin Trans. 1; 2000; p. 659-665.
Lichtenthaler et al.; "Hydroxymethyl-verzweigte Cyclanole durch Dialdehyd-Cyclisierung mit 2-Nitro-äthanol"; European Journal of Inorganic Chemistry; vol. 101 Issue 5; 1968; p. 1815-1818 (Contains English Abstract).
Zen et al.; "Synthetic Reactions of Aliphate Nitro-Compounds III, The Synthesis and Configurational Analysis of 2-Hydroxymethyl-2-aminocyclohexanediol"; Bulletin of the Chemical Society of Japan; vol. 42; Jun. 1969; p. 1761-1762.
Wang et al., Alternative Copolymerization of a Conjugated Segment and a Flexible Segment and Fabrication of a Fluorescent Sensing Film for HCl in the Vapor Phase; Chemistry an Asian Journal; vol. 8; 2013; p. 101-07.

(Continued)

*Primary Examiner* — Timothy R Rozof
(74) *Attorney, Agent, or Firm* — Baker & Hostetler LLP

(57) ABSTRACT

Described herein is a compound having the structure of formula I, II, or III,

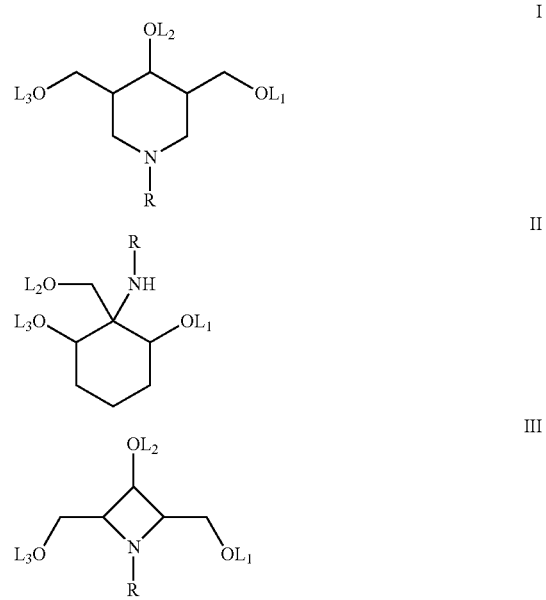

wherein R comprises a double stranded RNA molecule, and $L_1$, $L_2$, and $L_3$ independently for each occurrence comprise a ligand selected from the group consisting of a carbohydrate, a cholesteryl, or a peptide; a pharmaceutically accepted salt or pharmaceutical composition thereof; and a method of making the compound.

19 Claims, 27 Drawing Sheets

(56) References Cited

OTHER PUBLICATIONS

Wang et al.; "Cholestrol modified OPE functionalized film: fabrication, fluorescence behavior and sensing performance"; Journal of Materials Chemistry; vol. 22; 2012; p. 7529-7536.
Wang et al., "Synthesis and Characterisation of new types of side chain cholesteryl polymers"; Steroids; vol. 76; 2011; 6 pages.
Jensen et al.; "PET imaging of liposomes labeled with an [18F]-fluorocholesteryl ether probe prepared by automated radiosynthesis"; Journal of Liposome Research; vol. 22 No. 4; 2012; p. 295-305.
Winkler et al.; "Oligonucleotide conjugates for therapeutic applications"; Therapeutic Delivery; vol. 4 No. 7; Jul. 2013; p. 791-809.
International Patent Application No. PCT/US2016/044921; Int'l Search Report and the Written Opinion; dated Nov. 2, 2016; 12 pages.

MULTILIGAND AGENT FOR DRUG DELIVERY

CROSS REFERENCE TO RELATED APPLICATIONS

This application claims benefit under 35 U.S.C. § 119(e) of U.S. provisional patent application No. 62/199,577, filed Jul. 31, 2015, the content of which is incorporated herein by reference in its entirety.

TECHNICAL FIELD

What is described is a molecular agent that facilitates the intracellular delivery of a biologically active, therapeutic molecule. The molecular agent consists of a synthetic C4 or C6 cyclic aminotriol that is covalently linked to the biologically active molecule and at least two ligands. The molecular agent is suited for stereospecific presentation of the ligands to targeted cells. A pharmaceutical composition that comprises the molecular agent is useful to deliver therapeutically effective amounts of biologically active molecules into the cells of patients.

BACKGROUND

The delivery of a therapeutic compound to a subject is important for its therapeutic effects and is usually impeded by a limited ability of the compound to reach targeted cells and tissues. Improvement of such compounds to enter the targeted cells of tissues by a variety of means of delivery is crucial.

Examples of biologically active molecules for which effective targeting to a patient's tissues is often not achieved include numerous proteins including immunoglobulin proteins, polynucleotides such as genomic DNA, cDNA, mRNA, and siRNA, antisense polynucleotides; and many low molecular weight compounds, synthetic or naturally occurring, such as the peptide hormones and antibiotics.

Efficient delivery to cells in vivo requires specific targeting such as provided by conjugating a targeting ligand to the biologically active molecule. The targeting ligand provides specificity by assisting in receptor binding at the required target cell or tissue. A targeting ligand can also mediate receptor-mediated endocytosis at the target site by which the biologically active molecule bound to a membrane receptor is enveloped by the membrane via invagination of the membrane structure or by fusion of the delivery system with the cell membrane. Examples of receptor-mediated endocytotic systems are those that recognize sugars such as galactose, mannose, mannose-6-phosphate; or peptides and proteins such as transferrin, asialoglycoprotein, insulin and epidermal growth factor.

The asialoglycoprotein receptor (ASGP-R) on hepatic cells was identified and characterized on the basis of its ability to bind β-linked galactose or N-acetylgalactosamine (GalNAc) residues on proteins. ASGP-R consists of ASGR1 and ASGR2 subunits forming a variety of multimers that import large molecules across the cellular plasma membrane by endocytosis, a characteristic that makes it a potential target for receptor-mediated drug delivery to hepatocytes and hepatoma cells. A multivalent ligand consisting of several GalNAc molecules can achieve nanomolar affinity. Spacing and orientation among the sugar of the multivalent ligand affects binding. Lipophilic ligands, such as cholesterol or fatty acids can enhance plasma protein binding and consequently circulation half-life, and bind to plasma proteins such as lipoproteins. These ligands also can increase uptake in specific tissues expressing the corresponding lipoprotein receptor.

There remains an unmet need for a receptor-specific multiligand delivery agent and methods for its preparation to improve in vivo delivery of bioactive molecules.

SUMMARY

One aspect of what is described herein is a compound consisting of an aminotriol of formula I, II, or III,

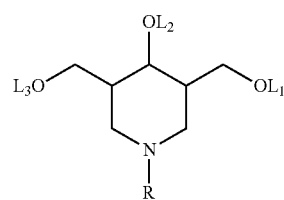

I

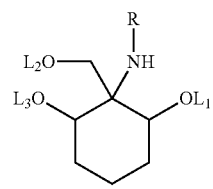

II

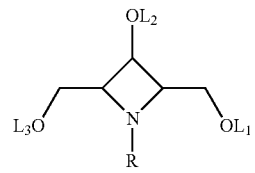

III wherein R comprises a biologically active molecule, and $L_1$, $L_2$, and $L_3$ independently for each occurrence comprise a ligand selected from the group consisting of a carbohydrate, a polypeptide, or a lipophile. The aminotriol of formula I may have the structure of formula Ia, Ib, or Ic

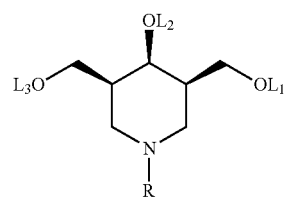

Ia

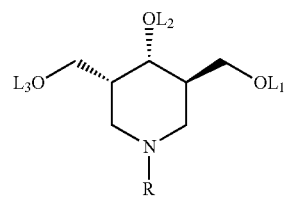

Ib

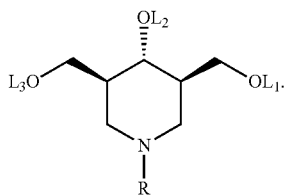

The aminotriol of formula II may have the structure of formula IIa

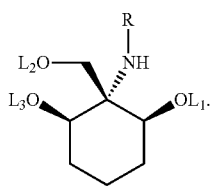

The aminotriol of formula III structure of formula IIIa, IIIb, or IIIc.

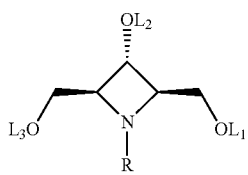

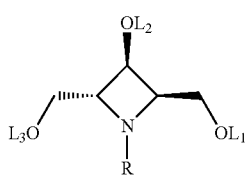

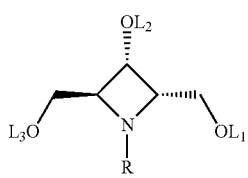

The biologically active molecule preferably is a therapeutic molecule, more preferably selected from an antibody, a polynucleotide, a hormone, an antibiotic, or a drug having a molecular weight less than 1000 Daltons. Most preferably, the biologically active molecule is a RNA molecule. The RNA molecule may consist of a sense and an antisense strand. The aminotriol may be covalently attached at the 3'-end of the sense strand, the 5'-end of the sense strand, the 3'-end of the antisense strand, or the 5'-end of the sense strand. The RNA molecule may comprises modified nucleotides, e.g., at least one UNA.

R preferably further comprises a phosphate moiety having the structure —O—P(Z')(Z")—O—, wherein Z' and Z" are independently for each occurrence O or S, and wherein the phosphate moiety is covalently attached to a 3'-end or 5'-end of the RNA molecule. One or more of R, $L_1$, $L_2$, or $L_3$ preferably further comprises a linker comprising the structure -(A-B$^1$—Z)$_n$-D$^1$- or

-D$^1$-B$^1$-D$^{1'}$-E-D$^{2'}$-B$^2$-D$^2$- wherein

A, D$^1$, D$^{1'}$, D$^2$, D$^{2'}$ are independently for each occurrence absent, CO, NH, O, S, OC(O), NHC(O), CH$_2$, CH$_2$NH, or CH$_2$O;

B$^1$ and B$^2$ are for each occurrence absent, alkylene, substituted alkylene wherein one or more methylenes can be interrupted or terminated by one or more of O, S, S(O), SO$_2$, N(R$^N$), C(R')=C(R"), C≡C, or C(O), wherein R' and R" are each independently H, $C_1$-$C_6$ alkyl, OH, SH, or N(R$^N$)$_2$, and R$^N$ is for each occurrence independently methyl, ethyl, propyl, isopropyl, butyl, or benzyl;

Z is absent, NH, O, S, CH$_2$, C(O)O, C(O)NH, NHCH(R$^a$)C(O), C(O)CH(R$^a$)NH, CO, CH=NO, or heterocyclyl, wherein R$^a$ is H or an amino acid side chain;

E is —CH$_2$N(E$^L$)CH$_2$—, wherein E$^L$ is -D$^3$-B$^3$-D$^{3'}$-R$^x$, wherein D$^3$ and D$^{3'}$ are each independently for each occurrence absent, CO, NH, O, S, OC(O), OC(O)O, NHC(O), NHC(O)NH, NHC(O)O, CH$_2$, CH$_2$NH or CH$_2$O, and R$^x$ is a cholesteryl or a cationic lipid; and n is 0, 1, 2, 3, 4, 5, 6, 7, 8, 9, 10, 11, 12, 13, 14, 15, 16, 17, 18, 19, or 20.

The linker of the one or more of R, $L_1$, $L_2$, or $L_3$ described above may further comprise an aminotriol of formula IV, V, or VI,

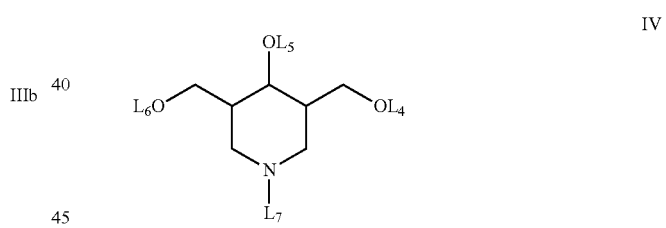

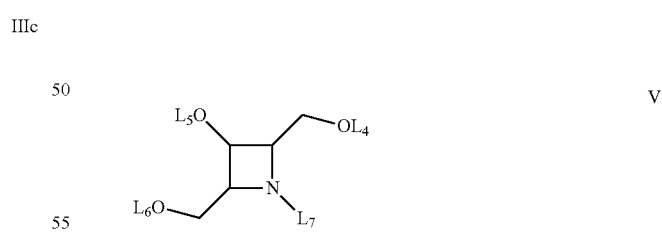

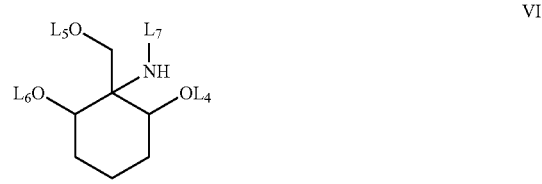

wherein $L_4$, $L_5$, $L_6$, and $L_7$ independently for each occurrence comprise a the structure -(A-B¹—Z)$_n$-D¹- or

-D¹-B¹-D¹'-E-D²'-B²-D²- wherein

A, $D^1$, $D^{1'}$, $D^2$, $D^{2'}$ are independently for each occurrence absent, CO, NH, O, S, OC(O), NHC(O), $CH_2$, $CH_2NH$, or $CH_2O$;

$B^1$ and $B^2$ are for each occurrence absent, alkylene, substituted alkylene wherein one or more methylenes can be interrupted or terminated by one or more of O, S, S(O), $SO_2$, $N(R^N)$, C(R')=C(R"), C≡C, or C(O), wherein R' and R" are each independently H, $C_1$-$C_6$ alkyl, OH, SH, or $N(R^N)_2$, and $R^N$ is for each occurrence independently methyl, ethyl, propyl, isopropyl, butyl, or benzyl;

Z is absent, NH, O, S, $CH_2$, C(O)O, C(O)NH, NHCH($R^a$)C(O), C(O)CH($R^a$)NH, CO, CH=NO, or heterocyclyl, wherein $R^a$ is H or an amino acid side chain;

E is —$CH_2N(E^L)CH_2$—, wherein $E^L$ is -$D^3$-$B^3$-$D^{3'}$-$R^x$, wherein $D^3$ and $D^{3'}$ are each independently for each occurrence absent, CO, NH, O, S, OC(O), OC(O)O, NHC(O), NHC(O)NH, NHC(O)O, $CH_2$, $CH_2NH$, or $CH_2O$, and $R^x$ is a cholesteryl or a cationic lipid; and n is 0, 1, 2, 3, 4, 5, 6, 7, 8, 9, 10, 11, 12, 13, 14, 15, 16, 17, 18, 19, or 20.

One or more of $L_1$, $L_2$, and $L_3$ may comprise a lipophile. The lipophile is selected from cholesterol, cholic acid, adamantane acetic acid, 1-pyrene butyric acid, dihydrotestosterone, 1,3-bis-O(hexadecyl)glycerol, geranyloxyhexyl group, hexadecylglycerol, borneol, menthol, 1,3-propanediol, heptadecyl group, palmitic acid, myristic acid, O-3-(oleoyl)lithocholic acid, O-3-(oleoyl)cholenic acid, dimethoxytrityl, and phenoxazine. A preferable lipophile is a cholesteryl, e.g., cholesterol.

One or more of $L_1$, $L_2$, and $L_3$ comprise a carbohydrate. The carbohydrate preferably is a monosaccharide selected from N-acetyl-galactosamine (GalNAc), allose, altrose, arabinose, cladinose, erythrose, erythrulose, fructose, D-fucitol, L-fucitol, fucosamine, fucose, fuculose, galactosamine, D-galactosaminitol, galactose, glucosamine, N-acetyl-glucosamine, glucosaminitol, glucose, glucose-6-phosphate, gulose glyceraldehyde, L-glycero-D-mannos-heptose, glycerol, glycerone, gulose, idose, lyxose, mannosamine, mannose, mannose-6-phosphate, psicose, quinovose, quinovosamine, rhamnitol, rhamnosamine, rhamnose, ribose, ribulose, sedoheptulose, sorbose, tagatose, talose, tartaric acid, threose, xylose and xylulose. The monosaccharide preferably is in a D- or L configuration. Preferably, the carbohydrate is GalNAc or D-galactose.

The monosaccharide may be selected from a deoxy sugar, an amino sugar, a thio sugar, a seleno sugar, a telluro sugar, an aza sugar, an imino sugar, a phosphano sugar, a phospha sugar, a C-substituted monosaccharide, an unsaturated monosaccharide, an alditol, aldonic acid, a ketoaldonic acid, a uronic acid, or an aldaric acid.

The carbohydrate may be a disaccharide, trisaccharide or polysaccharide comprising abequose, acrabose, anucetose, amylopectin, amylose, apiose, arcanose, ascarylose, ascorbic acid, boivinose, cellobiose, cellobiose, cellulose, chacotriose, chalcose, chitin, colitose, cyclodextrin, cymarose, dextrin, 2-deoxyribose, 2deoxyglucose, diginose, digitalose, digitoxose, evalose, evemitrose, fructooligosachharide, galto-oligosaccharide, gentianose, gentiobiose, glucan, glucogen, glycogen, hamamelose, heparin, inulin, isolevoglucosenone, isomaltose, isomaltotriose, isopanose, kojibiose, lactose, lactosamine, lactosediamine, laminarabiose, levoglucosan, levoglucosenone, β-maltose, maltriose, mannan-oligosaccharide, manninotnose, melezitose, melibiose, muramic acid, mycarose, mycinose, neuraminic acid, nigerose, nojirimycin, noviose, oleandrose, panose, paratose, planteose, pnmeverose, raffinose, rhodinose, rutinose, sarmentose, sedoheptulose, sedoheptulosan, solatriose, sophorose, stachyose, streptose, sucrose, am-trehalose, trehalosamine, turanose, tyvelose, xylobiose, or umbelliferose.

$L_1$, $L_2$, and/or $L_3$ may comprise a polypeptide. The polypeptide may be a ligand for a cellular receptor, e.g., is arginylglycylaspartic acid (RGD) or a ligand for the transferrin receptor (TfR) comprising a TfR-binding domain of transferrin. The polypeptide may be an antibody.

$L_1$, $L_2$, and $L_3$ may independently comprise a linker consisting of

-(A-B—Z)$_n$-D-, wherein

A and D are independently for each occurrence absent, CO, NH, O, S, OC(O), NHC(O), $CH_2$, $CH_2NH$, or $CH_2O$;

B is absent, alkylene, substituted alkylene wherein one or more methylenes can be interrupted or terminated by one or more of O, S, S(O), $SO_2$, $N(R^N)$, C(R')=C(R"), C≡C or C(O), wherein R' and R" are each independently H, $C_1$-$C_6$ alkyl, OH, SH or $N(R^N)_2$, and $R^N$ is for each occurrence independently methyl, ethyl, propyl, isopropyl, butyl, or benzyl;

Z is absent, NH, O, S, $CH_2$, C(O)O, C(O)NH, NHCH($R^a$)C(O), C(O)CH($R^a$)NH, CO, CH=NO, or heterocyclyl, wherein $R^a$ is H or an amino acid side chain; and n is 0, 1, 2, 3, 4, 5, 6, 7, 8, 9, 10, 11, 12, 13, 14, 15, 16, 17, 18, 19, or 20.

$L_2$, or $L_3$, or both may comprise a linker that comprises a polyethylene glycol. Preferably, $L_2$, or $L_3$, or both comprise a linker that comprises an amide linkage. More preferably, $L_2$, or $L_3$, or both comprise a linker comprising —O(CH$_2$)$_4$(CO)NH(CH$_2$)$_3$NH(CO)(CH$_2$)$_2$O— and the ligand is GalNAc. Preferably, $L_1$ comprises a linker comprising —O(CH$_2$)$_{10}$O— and the ligand is cholesterol. Most preferably $L_1$ comprises a linker comprising —O(CH$_2$)$_{10}$O—, the $L_1$ ligand is cholesterol, and both $L_2$ and $L_3$ comprise a linker comprising —O(CH$_2$)$_4$(CO)NH(CH$_2$)$_3$NH(CO)(CH$_2$)$_2$O— and the associated ligand is GalNAc.

Another aspect of the description is a process of making a multiligand compound shown formula 45,

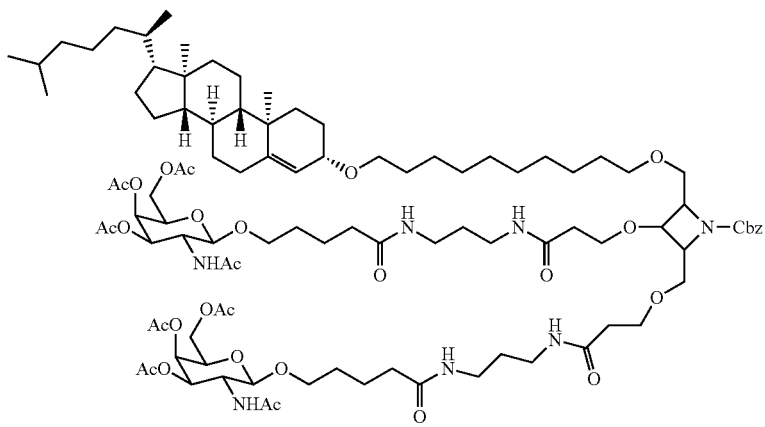

the process comprising the steps of
i. reacting aminotriol compound

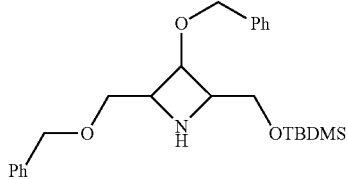 [SMILES: CC(C)(C)[Si](C)(C)OCC1NC(COCc2ccccc2)C1OCc1ccccc1]

with a lipophile 42

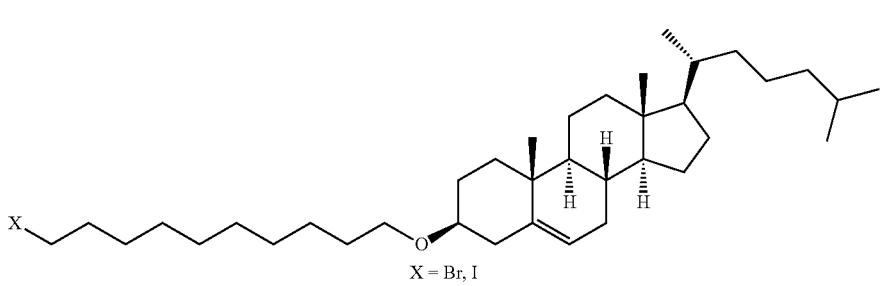

ii. removing hydroxyl protecting groups from the product of step i;

iii. reacting the product of step ii with (CHCH)COO-t-butyl in NaOH;

iv. adding an amino protecting group to the product of step iii;

v. reacting the product of step iv with BocN(CH$_2$)$_3$NH$_2$ using 1-ethyl-3-(3-dimethylaminopropyl)carbodiimide-hydrochloride (EDC) and hydroxybenzotriazole (HOBT);

vi. reacting the product of step v with GalNAc acid

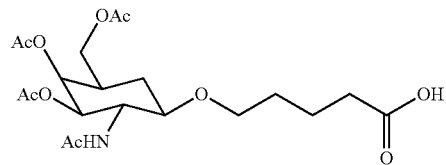 [SMILES: CC(=O)NC1C(OCCCCC(=O)O)CC(COC(C)=O)C(OC(C)=O)C1OC(C)=O]

using EDC, HOBT, and N,N-diisopropylethylamine.

The starting material for the process preferably is an aminotriol having the structure of formula 1, 5, or 9

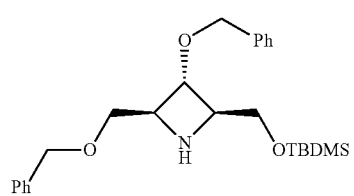

-continued

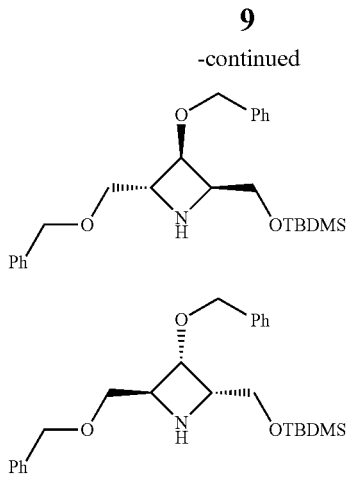

Another aspect of the description is process of making a multiligand compound shown formula 53 i. reacting aminotriol compound

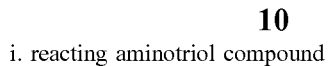

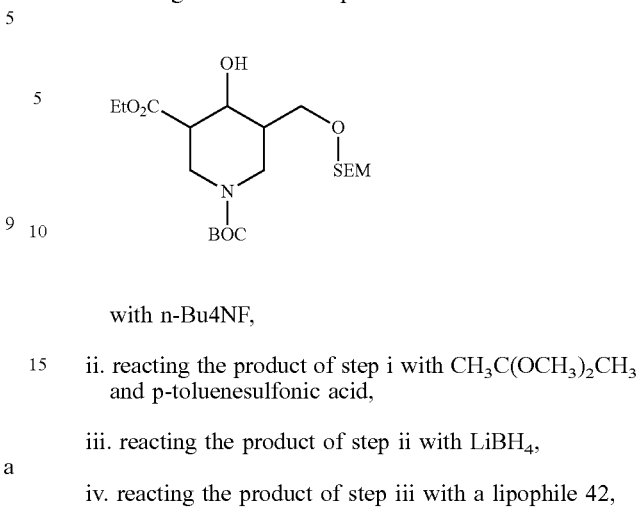

with n-Bu4NF, ii. reacting the product of step i with $CH_3C(OCH_3)_2CH_3$ and p-toluenesulfonic acid, iii. reacting the product of step ii with $LiBH_4$, iv. reacting the product of step iii with a lipophile 42,

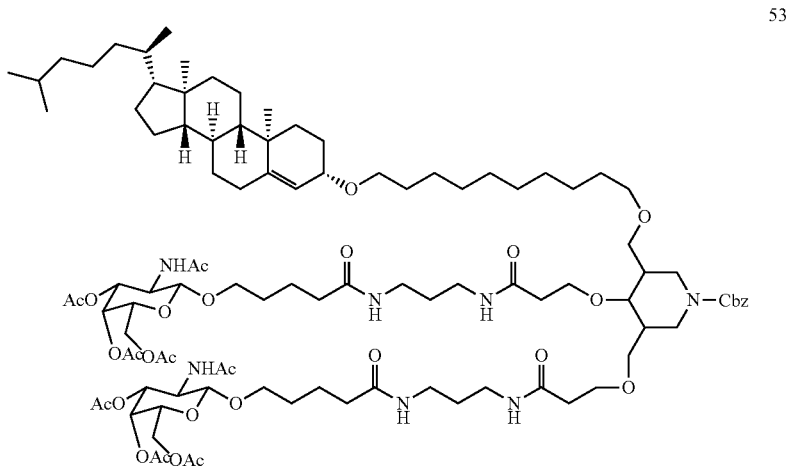

the process comprising the steps of

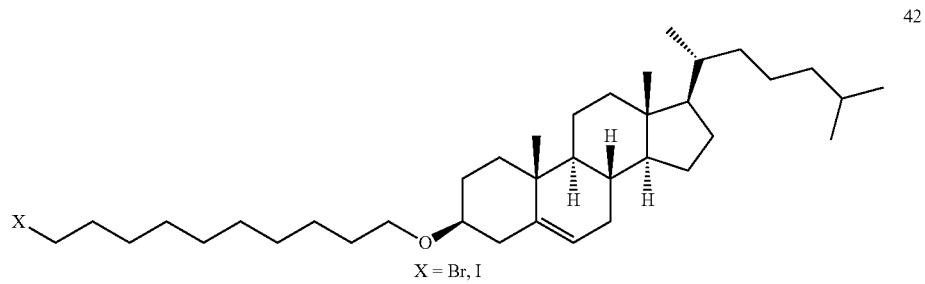

v. removing hydroxyl protecting groups from the product of step iv;

vi. reacting the product of step v with (CHCH)COO-t-butyl in NaOH;

vii. adding an amino protecting group to the product of vi;

viii. reacting the product of step viii with BocN(CH$_2$)$_3$NH$_2$ using EDC and HOBT;
ix. reacting the product of step ix with GalNAc acid

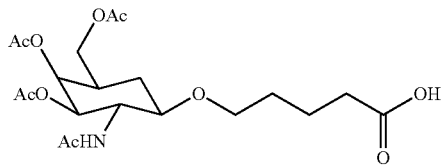 [SMILES: CC(=O)NC1C(OCCCCC(=O)O)CC(COC(C)=O)C(OC(C)=O)C1OC(C)=O]

11 using EDC, HOBT, and N,N-diisopropylethylamine.
The process preferably starts with an aminotriol compound having the structure of formula 13, 19, or 30.

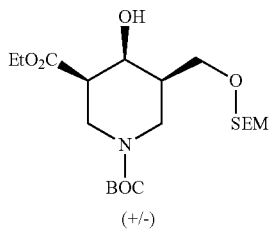

13
(+/-)

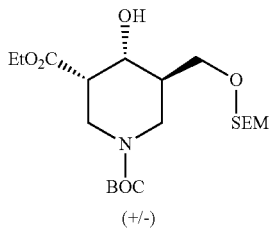

19
(+/-)

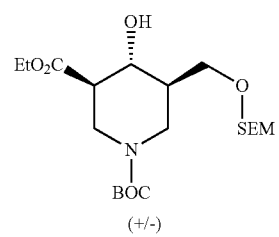

30
(+/-)

Another aspect of the description is process of making a multiligand compound shown formula 45,

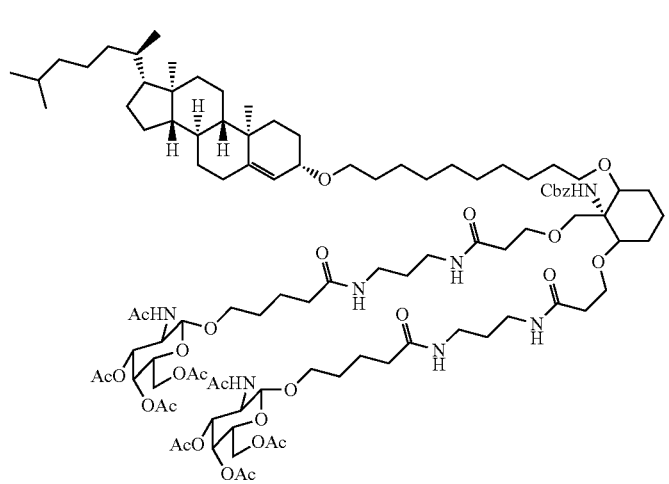

45 the process comprising the steps of
i. reacting aminotriol compound having formula 38

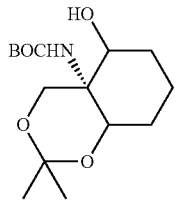

38 with a lipophile 42,

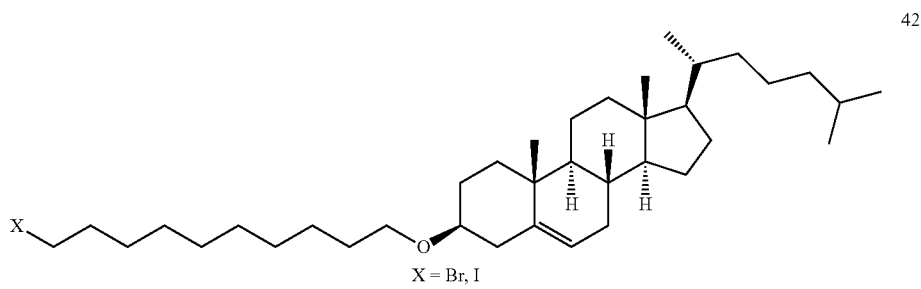

42

X = Br, I ii. removing hydroxyl protecting groups from the product of step i;
iii. reacting the product of step ii with (CHCH)COO-t-butyl in NaOH;
iv. adding an amino protecting group to the product of step iii;
v. reacting the product of step iv with BocN(CH$_2$)$_3$NH$_2$ using EDC and HOBT;
vi. reacting the product of step v with GalNAc acid

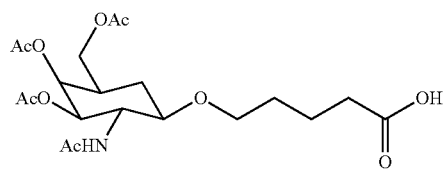 [SMILES: CC(=O)NC1C(OCCCCC(=O)O)CC(COC(C)=O)C(OC(C)=O)C1OC(C)=O]

using EDC, HOBT, and N,N-diisopropylethylamine.

Another aspect of the description is a pharmaceutical composition comprising a compound consisting of an aminotriol of formula I, II, or III,

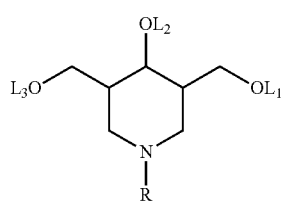

I

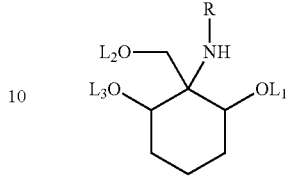

II

-continued

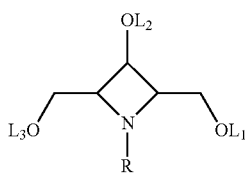

III wherein R comprises a therapeutic molecule, and L$_1$, L$_2$, and L$_3$ independently for each occurrence comprise a ligand selected from the group consisting of a carbohydrate, a polypeptide, or a lipophile. The pharmaceutical composition may further comprise a pharmaceutically acceptable counterion or a pharmaceutically acceptable excipient. Preferably, the therapeutic molecule is an RNA, more preferably a double-stranded siRNA. The double-stranded siRNA may comprise a UNA. Preferably the L$_2$ and L$_3$ ligand are a carbohydrate, most preferably, GalNAc or galactose.

Another aspect of the description is a method of treating a disease comprising administering a therapeutically effective amount of a pharmaceutical composition comprising a compound consisting of an aminotriol of formula I, II, or III,

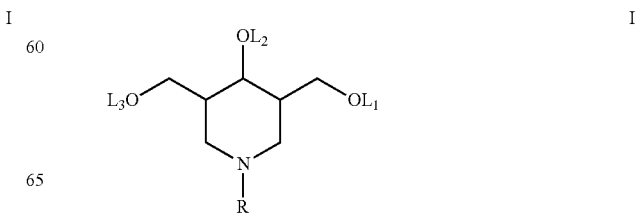

I

-continued

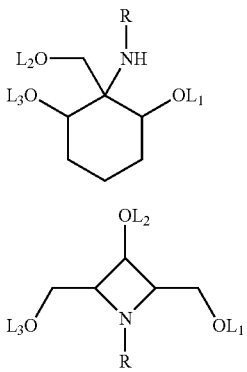

wherein R comprises a therapeutic molecule, and $L_1$, $L_2$, and $L_3$ independently for each occurrence comprise a ligand selected from the group consisting of a carbohydrate, a polypeptide, or a lipophile. The compound may comprise an RNA that knocks down expression of a target gene, e.g., Factor VII, Eg5, PCSK9, TPX2, apoB, SAA, TTR, RSV, PDGF beta, Erb-B, Src, CRK, GRB2, RAS, MEKK, JNK, RAF, Erk1/2, PCNA (p21), MYB, JUN, FOS, BCL-2, Cyclin D, VEGF, EGFR, Cyclin A, Cyclin E, WNT-1, beta-catenin, c-MET, PKC, NFKB, STAT3, survivin, Her2/Neu, topoisomerase I, or topoisomerase II alpha; or a mutant gene of p73, p21(WAF1/CIP1), p27(KIP1), PPM1D, RAS, caveolin I, MIB I, MTAI, M68, or p53 tumor suppressor. The pharmaceutical composition preferably is administered subcutaneously.

DETAILED DESCRIPTION

Figure 1:
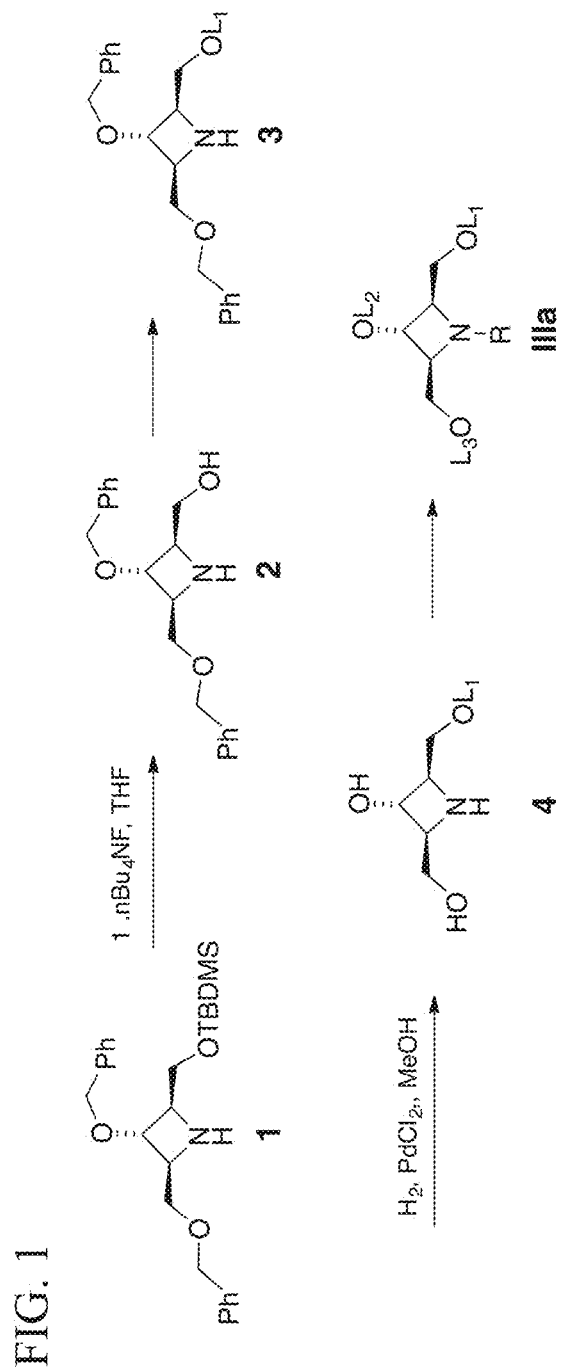
FIG. 1 shows equation (1) for the synthesis of the aminotriol of formula IIIa.

What is described herein is a multiligand agent for delivery of a therapeutic molecule to a target cell in a subject's body following subcutaneous administration.

The multiligand agent comprises the therapeutic molecule as a covalently conjugated substituent. A preferred therapeutic molecule is a biologically active polynucleotide or oligonucleotide, such as fragments of genomic DNA, mRNA, DNA copies of mRNA (cDNA), double-stranded short interfering RNA (siRNA), partially double-stranded short hairpin RNA (shRNA), single stranded antisense RNA, or microRNA (miRNA). More preferably the therapeutic molecule is a siRNA that is capable of knocking down expression of a target gene by interfering with mRNA function upon entry into a cell expressing the target gene encoding the mRNA that is complementary to the sequence of one strand of the siRNA. The oligonucleotide can be 10-10,000 nucleotides in length (nt), 10-1,000 nt, 10-500 nt, preferably 15-100 nt, most preferably 15-35 nt.

The multiligand agent also comprises a set of ligands. In biochemistry and pharmacology, a ligand is a substance that forms a complex with a biomolecule to serve a biological purpose. In protein-ligand binding, the ligand is usually a signal-triggering molecule, binding to a site on a target protein. The binding occurs by intermolecular forces, such as ionic bonds, hydrogen bonds and van der Waals forces. The docking (association) is usually reversible (dissociation), and is characterized by a dissociation constant ($K_D$). The value of $K_D$ is inversely related to the strength of binding (affinity) between the ligand and receptor so that the smaller the value of $K_D$, the higher the affinity of the ligand to the receptor. Ligands include substrates, inhibitors, activators, and neurotransmitters. Ligand binding is often characterized in terms of the concentration of ligand at which half of the receptor binding sites are occupied, known as the IC50, which is related to but different from the dissociation constant. By possessing more than one ligand, the multiligand agent binds much more strongly (i.e., has a lower value of $K_D$) than the single ligand alone. The increase in affinity of a multiligand agent is substantially greater than a monoligand.

The multiligand agent described herein is a compound consisting of an aminotriol of formula I, II, or III,

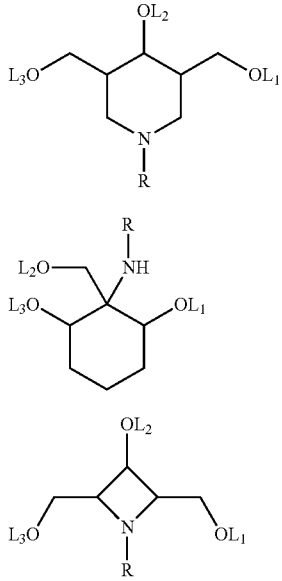

wherein R comprises a biologically active molecule, and $L_1$, $L_2$, and $L_3$ independently for each occurrence comprise a ligand selected from the group consisting of a carbohydrate, a polypeptide, or a lipophile.

The aminotriol of formula I, may have the structure of formula Ia, Ib, or Ic

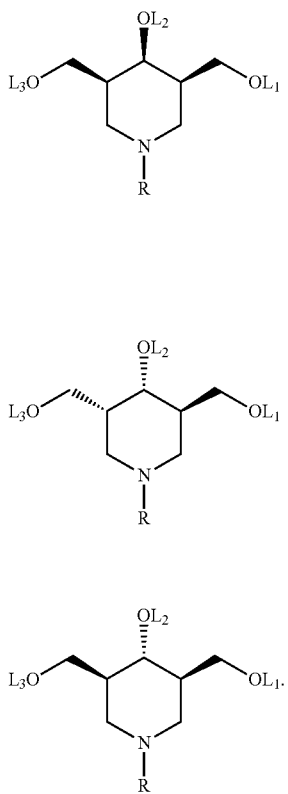

The aminotriol of formula II may have the structure of formula IIa

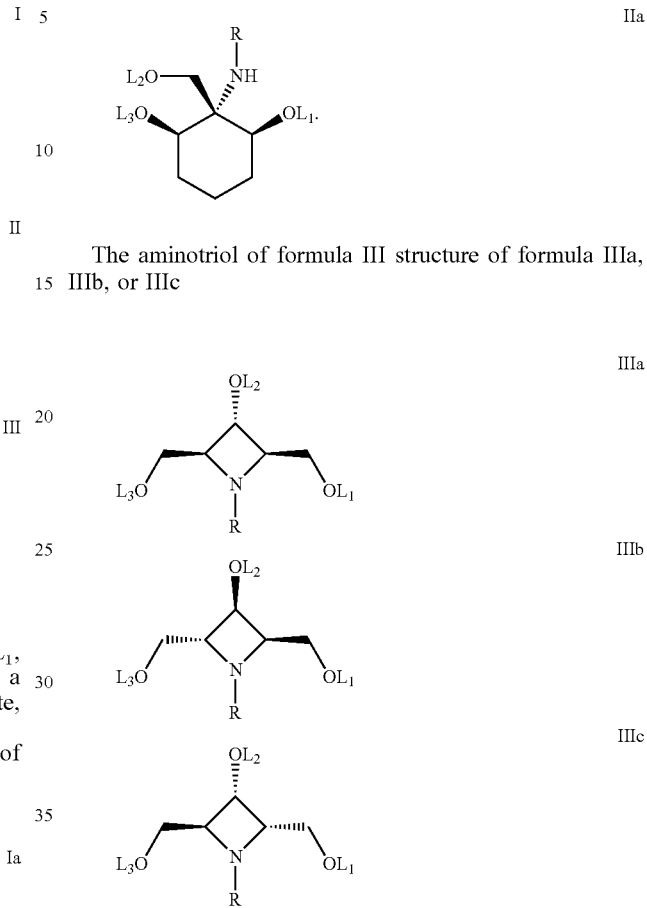

The aminotriol of formula III structure of formula IIIa, IIIb, or IIIc

The biologically active molecule preferably is a therapeutic molecule, more preferably selected from an antibody, a polynucleotide, a hormone, an antibiotic, or a drug having a molecular weight less than 1000 Daltons. Most preferably, the biologically active molecule is a RNA molecule. The RNA molecule may consist of a sense and an antisense strand. The aminotriol may be covalently attached at the 3'-end of the sense strand, the 5' end of the sense strand, the 3' end of the antisense strand, or the 5' end of the sense strand. The RNA molecule may comprises modified nucleotides, e.g., at least one UNA.

R preferably further comprises a phosphate moiety having the structure —O—P(Z')(Z")—O—, wherein Z' and Z" are independently for each occurrence O or S, and wherein the phosphate moiety is covalently attached to a 3'-end or 5'-end of the RNA molecule. One or more of R, $L_1$, $L_2$, or $L_3$ preferably further comprises a linker comprising the structure -(A-B$^1$—Z)$_n$-D$^1$- or

-D$^1$-B$^1$-D$^{1'}$-E-D$^{2'}$-B$^2$-D$^2$- wherein
A, D$^1$, D$^{1'}$, D$^2$, D$^{2'}$ are independently for each occurrence absent, CO, NH, O, S, OC(O), NHC(O), CH$_2$, CH$_2$NH, or CH$_2$O;
B$^1$ and B$^2$ are for each occurrence absent, alkylene, substituted alkylene wherein one or more methylenes can be interrupted or terminated by one or more of O, S, S(O), SO$_2$, N(R$^N$), C(R')=C(R"), C≡C, or C(O), wherein R' and R" are each independently H, C$_1$-C$_6$ alkyl, OH, SH, or N(R$^N$)$_2$, and R$^N$ is for each occurrence independently methyl, ethyl, propyl, isopropyl, butyl, or benzyl;

Z is absent, NH, O, S, CH$_2$, C(O)O, C(O)NH, NHCH(R$^a$)C(O), C(O)CH(R$^a$)NHCO, CH=NO, or heterocyclyl, wherein R$^a$ is H or an amino acid side chain;

E is —CH$_2$N(E$^L$)CH$_2$—, wherein E$^L$ is -D$^3$-B$^3$-D$^{3'}$-R$^x$, wherein D$^3$ and D$^{3'}$ are each independently for each occurrence absent, CO, NH, O, S, OC(O), OC(O)O, NHC(O), NHC(O)NH, NHC(O)O, CH$_2$, CH$_2$NH, or CH$_2$O, and R$^x$ is a cholesteryl or a cationic lipid; and n is 0, 1, 2, 3, 4, 5, 6, 7, 8, 9, 10, 11, 12, 13, 14, 15, 16, 17, 18, 19, or 20.

The linker may further comprise an aminotriol of formula IV, V, or VI,

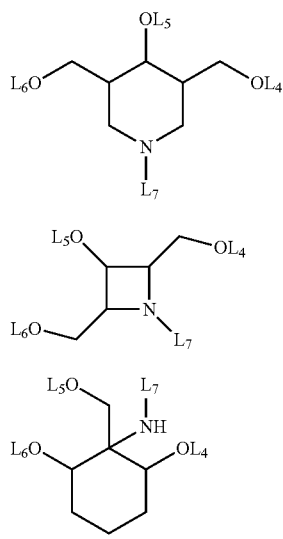

wherein L$_4$, L$_5$, L$_6$, and L$_7$ independently for each occurrence comprise a the structure -(A-B$^1$—Z)$_n$-D$^1$- or

-D$^1$-B$^1$-D$^{1'}$-E-D$^{2'}$-B$^2$-D$^2$- wherein

A, D$^1$, D$^{1'}$, D$^2$, D$^{2'}$ are independently for each occurrence absent, CO, NH, O, S, OC(O), NHC(O), CH$_2$, CH$_2$NH, or CH$_2$O;

B$^1$ and B$^2$ are for each occurrence absent, alkylene, substituted alkylene wherein one or more methylenes can be interrupted or terminated by one or more of O, S, S(O), SO$_2$, N(R$^N$), C(R')=C(R"), C≡C, or C(O), wherein R' and R" are each independently H, C$_1$-C$_6$ alkyl, OH, SH, or N(R$^N$)$_2$, and R$^N$ is for each occurrence independently methyl, ethyl, propyl, isopropyl, butyl or benzyl;

Z is absent, NH, O, S, CH$_2$, C(O)O, C(O)NH, NHCH(R$^a$)C(O), C(O)CH(R$^a$)NH, CO, CH=NO, or heterocyclyl, wherein R$^a$ is H or an amino acid side chain;

E is —CH$_2$N(E$^L$)CH$_2$—, wherein E$^L$ is -D$^3$-B$^3$-D$^{3'}$-R$^x$, wherein D$^3$ and D$^{3'}$ are each independently for each occurrence absent, CO, NH, O, S, OC(O), OC(O)O, NHC(O), NHC(O)NH, NHC(O)O, CH$_2$, CH$_2$NH, or CH$_2$O, and R$^x$ is a cholesteryl or a cationic lipid; and n is 0, 1, 2, 3, 4, 5, 6, 7, 8, 9, 10, 11, 12, 13, 14, 15, 16, 17, 18, 19, or 20.

One or more of L$_1$, L$_2$, and L$_3$ may comprise a lipophile. The lipophile is selected from cholesterol, cholic acid, adamantane acetic acid, 1-pyrene butyric acid, dihydrotestosterone, 1,3-bis-O(hexadecyl)glycerol, geranyloxyhexyl group, hexadecylglycerol, borneol, menthol, 1,3-propanediol, heptadecyl group, palmitic acid, myristic acid, O-3-(oleoyl)lithocholic acid, O-3-(oleoyl)cholenic acid, dimethoxytrityl, and phenoxazine. A preferable lipophile is a cholesteryl, e.g., cholesterol.

One or more of L$_1$, L$_2$, and L$_3$ comprise a carbohydrate. The carbohydrate preferably is a monosaccharide selected from GalNAc, allose, altrose, arabinose, cladinose, erythrose, erythrulose, fructose, D-fucitol, L-fucitol, fucosamine, fucose, fuculose, galactosamine, D-galactosaminitol, galactose, glucosamine, N-acetyl-glucosamine, glucosaminitol, glucose, glucose-6-phosphate, gulose glyceraldehyde, L-glycero-D-mannos-heptose, glycerol, glycerone, gulose, idose, lyxose, mannosamine, mannose, mannose-6-phosphate, psicose, quinovose, quinovosamine, rhamnitol, rhamnosamine, rhamnose, ribose, ribulose, sedoheptulose, sorbose, tagatose, talose, tartaric acid, threose, xylose and xylulose. The monosaccharide preferably is in a D- or L configuration. The monosaccharide may be selected from a deoxy sugar, an amino sugar, a thio sugar, a seleno sugar, a telluro sugar, an aza sugar, an imino sugar, a phosphano sugar, a phospha sugar, a C-substituted monosaccharide, an unsaturated monosaccharide, an alditol, aldonic acid, a ketoaldonic acid, a uronic acid, or an aldaric acid. The carbohydrate may be a disaccharide, trisaccharide or polysaccharide comprising abequose, acrabose, anucetose, amylopectin, amylose, apiose, arcanose, ascarylose, ascorbic acid, boivinose, cellobiose, cellobiose, cellulose, chacotriose, chalcose, chitin, colitose, cyclodextrin, cymarose, dextrin, 2-deoxyribose, 2deoxyglucose, diginose, digitalose, digitoxose, evalose, evemitrose, fructooligosachharide, galto-oligosaccharide, gentianose, gentiobiose, glucan, glucogen, glycogen, hamamelose, heparin, inulin, isolevoglucosenone, isomaltose, isomaltotriose, isopanose, kojibiose, lactose, lactosamine, lactosediamine, laminarabiose, levoglucosan, levoglucosenone, β-maltose, maltriose, mannan-oligosaccharide, manninotnose, melezitose, melibiose, muramic acid, mycarose, mycinose, neuraminic acid, nigerose, nojirimycin, noviose, oleandrose, panose, paratose, planteose, pnmeverose, raffinose, rhodinose, rutinose, sarmentose, sedoheptulose, sedoheptulosan, solatriose, sophorose, stachyose, streptose, sucrose, am-trehalose, trehalosamine, turanose, tyvelose, xylobiose, or umbelliferose. Preferably, the carbohydrate is GalNAc or D-galactose.

L$_1$, L$_2$, and/or L$_3$ may comprise a polypeptide. The polypeptide may be a ligand for a cellular receptor, e.g., is RGD or a ligand for the TfR comprising a TfR-binding domain of transferrin. The polypeptide may be an antibody.

L$_1$, L$_2$, and L$_3$ may independently comprise a linker consisting of

-(A-B—Z)$_n$-D-, wherein

A and D are independently for each occurrence absent, CO, NH, O, S, OC(O), NHC(O), CH$_2$, CH$_2$NH, or CH$_2$O;

B is absent, alkylene, substituted alkylene wherein one or more methylenes can be interrupted or terminated by one or more of O, S, S(O), SO$_2$, N(R$^N$), C(R')=C(R"), C≡C, or C(O), wherein R' and R" are each independently H, C$_1$-C$_6$ alkyl, OH, SH, or $N(R^N)_2$, and $R^N$ is for each occurrence independently methyl, ethyl, propyl, isopropyl, butyl or benzyl;

Z is absent, NH, O, S, $CH_2$, C(O)O, C(O)NH, $NHCH(R^a)$ C(O), $C(O)CH(R^a)NH$, CO, CH=NO, or heterocyclyl, wherein $R^a$ is H or an amino acid side chain; and n is 0, 1, 2, 3, 4, 5, 6, 7, 8, 9, 10, 11, 12, 13, 14, 15, 16, 17, 18, 19, or 20.

$L_2$, or $L_3$, or both may comprise a linker that comprises a polyethylene glycol. Preferably, $L_2$, or $L_3$, or both comprise a linker that comprises an amide linkage. More preferably, $L_2$, or $L_3$, or both comprise a linker comprising —$O(CH_2)_4$ $(CO)NH(CH_2)_3NH(CO)(CH_2)_2O$— and the ligand is GalNAc. Preferably, $L_1$ comprises a linker comprising —$O(CH_2)_{10}O$— and the ligand is cholesterol. Most preferably $L_1$ comprises a linker comprising —$O(CH_2)_{10}O$—, the $L_1$ ligand is cholesterol, and both $L_2$ and $L_3$ comprise a linker comprising —$O(CH_2)_4(CO)NH(CH_2)_3NH(CO)(CH_2)_2O$— and the associated ligand is GalNAc.

Definitions

"At least one" means one or more (e.g., 1-3, 1-2, or 1).

"Composition" includes a product comprising the specified ingredients in the specified amounts, as well as any product that results, directly or indirectly, from combination of the specified ingredients in the specified amounts.

"In combination with" as used to describe the administration of a compound of formulas 1, I, and II with other medicaments in the methods of treatment of this invention, means—that the compounds of formulas 1, I, and II and the other medicaments are administered sequentially or concurrently in separate dosage forms, or are administered concurrently in the same dosage form.

"Mammal" means a human or other mammal, or means a human being.

"Patient" includes both human and other mammals, preferably human.

"Alkyl" is a saturated or unsaturated, straight or branched, hydrocarbon chain. In various embodiments, the alkyl group has 1-18 carbon atoms, i.e. is a $C_1$-$C_{18}$ group, or is a $C_1$-$C_{12}$ group, a $C_1$-$C_6$ group, or a $C_1$-$C_4$ group. Independently, in various embodiments, the alkyl group has zero branches (i.e., is a straight chain), one branch, two branches, or more than two branches. "Alkenyl" is an unsaturated alkyl that may have one double bond, two double bonds, more than two double bonds. "Alkynal" is an unsaturated alkyl that may have one triple bond, two triple bonds, or more than two triple bonds. Alkyl chains may be optionally substituted with 1 substituent (i.e., the alkyl group is mono-substituted), or 1-2 substituents, or 1-3 substituents, or 1-4 substituents, etc. The substituents may be selected from the group consisting of hydroxy, amino, alkylamino, boronyl, carboxy, nitro, cyano, and the like. When the alkyl group incorporates one or more heteroatoms, the alkyl group is referred to herein as a heteroalkyl group. When the substituents on an alkyl group are hydrocarbons, then the resulting group is simply referred to as a substituted alkyl. In various aspects, the alkyl group including substituents has less than 25, 24, 23, 22, 21, 20, 19, 18, 17, 16, 15, 14, 13, 12, 11, 10, 9, 8, or 7 carbons.

"Lower alkyl" means a group having one to six carbon atoms in the chain which chain may be straight or branched. Non-limiting examples of suitable alkyl groups include methyl, ethyl, n-propyl, isopropyl, n-butyl, t-butyl, n-pentyl, and hexyl.

"Alkoxy" means an alkyl-O-group wherein alkyl is as defined above. Non-limiting examples of alkoxy groups include: methoxy, ethoxy, n-propoxy, isopropoxy, n-butoxy and heptoxy. The bond to the parent moiety is through the ether oxygen.

"Alkoxyalkyl" means an alkoxy-alkyl-group in which the alkoxy and alkyl are as previously described. Preferred alkoxyalkyl comprise a lower alkyl group. The bond to the parent moiety is through the alkyl.

"Alkylaryl" means an alkyl-aryl-group in which the alkyl and aryl are as previously described. Preferred alkylaryls comprise a lower alkyl group. The bond to the parent moiety is through the aryl.

"Aminoalkyl" means an $NH_2$-alkyl-group, wherein alkyl is as defined above, bound to the parent moiety through the alkyl group.

"Carboxyalkyl" means an HOOC-alkyl-group, wherein alkyl is as defined above, bound to the parent moiety through the alkyl group.

"Commercially available chemicals" and the chemicals used in the Examples set forth herein may be obtained from standard commercial sources.

"Compounds described in the chemical literature" may be identified through reference books and databases directed to chemical compounds and chemical reactions known to one of ordinary skill in the art. Suitable reference books and treatise that detail the synthesis of reactants useful in the preparation of compounds disclosed herein, or provide references to articles that describe the preparation of compounds disclosed herein, include, e.g., Wagner, SYNTHETIC ORGANIC CHEMISTRY, John Wiley, NY, 1953; Sandler, ORGANIC FUNCTIONAL GROUP PREPARATIONS, $2^{nd}$ Ed., Academic Press, NY, 1983; House, MODERN SYNTHETIC REACTIONS, $2^{nd}$ Ed., W A Benjamin, Menlo Park, Calif., 1972; Glichrist, HETEROCYCLIC CHEMISTRY, $2^{nd}$ Ed. John Wiley and Sons, NY, 1992; March, ADVANCED ORGANIC CHEMISTRY: REACTIONS, MECHANISMS AND STRUCTURE, $5^{th}$ Ed., Wiley Interscience, NY, 2001. The disclosures of these publications is hereby incorporated by reference into the present disclosure to more fully describe the state of the art to which this invention pertains.

"Halo" means fluoro, chloro, bromo, or iodo groups. Preferred are fluoro, chloro or bromo, and more preferred are fluoro and chloro.

"Halogen" means fluorine, chlorine, bromine, or iodine. Preferred are fluorine, chlorine and bromine.

"Heteroalkyl" is a saturated or unsaturated, straight or branched, chain containing carbon and at least one heteroatom. The heteroalkyl group may, in various embodiments, have on heteroatom, or 1 or 2 heteroatoms, or 1, 2 or 3 heteroatoms, or 1, e, 3, or 4 heteroatoms. In one aspect the heteroalkyl chain contains from 1, 2, 3, 4, 5, 6, 7, 8, 9, 10, 11, 12, 13, 14, 15, 16, 17, or 18 (i.e., 1-18) member atoms (carbon and heteroatoms), and in various embodiments contain 1, 2, 3, 4, 5, 6, 7, 8, 9, 10, 11, or 12 (1-12), or 1-6, or 1-4 member atoms. Independently, in various embodiments, the heteroalkyl group has no branches (i.e., is a straight chain), one branch, two branches, or more than two branches. Independently, in one embodiment, the hetereoalkyl group is saturated. In another embodiment, the heteroalkyl group is unsaturated. In various embodiments, the unsaturated heterolkyl may have one double bond, two double bonds, more than two double bonds, and/or one triple bond, two triple bonds, or more than two triple bonds. Heteroalkyl chains may be substituted or unsubstituted. In one embodiment, the heteroalkyl chain is unsubstituted. In another embodiment, the heteroalkyl chain is substituted. A substituted heteroalkyl chain may have 1 substituent (i.e., by monosubstituted), or may have, e.g., 1-2 substituents, or 1-3 substituents, or 1-4 substituents. Exemplary heteroalkyl substituents include esters (—C(O)OR) and carbonyls (—C(O)—).

"Hydroxyalkyl" means an HO-alkyl-group, in which alkyl is previously defined. Preferred hydroxyalkyls contain lower alkyl. Non-limiting examples of suitable hydroxyalkyl groups include hydroxymethyl and 2-hydroxyethyl.

"Hydrate" is a solvate wherein the solvent molecule is $H_2O$.

A "lipophilic molecule" and a "lipid" mean an organic compound that comprises an ester of fatty acid and is characterized by being insoluble in water, but soluble in many organic solvents. Lipids are usually divided into at least three classes: (1) "simple lipids," which include fats and oils as well as waxes; (2) "compound lipids," which include phospholipids and glycolipids; and (3) "derived lipids" such as steroids.

"Solvate" means a physical association of a compound of this disclosure with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like.

"Lipid encapsulated" can mean a lipid particle that provides a therapeutic nucleic acid such as an mRNA with full encapsulation, partial encapsulation, or both. In a preferred embodiment, the nucleic acid (e.g., mRNA) is fully encapsulated in the lipid particle.

"Lipid conjugate" means a conjugated lipid that inhibits aggregation of lipid particles. Such lipid conjugates include, but are not limited to, PEG-lipid conjugates such as, e.g., PEG coupled to dialkyloxypropyls (e.g., PEG-DAA conjugates), PEG coupled to diacylglycerols (e.g., PEG-DAG conjugates), PEG coupled to cholesterol, PEG coupled to phosphatidylethanolamines, and PEG conjugated to ceramides, cationic PEG lipids, polyoxazoline (POZ)-lipid conjugates, polyamide oligomers (e.g., ATTA-lipid conjugates), and mixtures thereof. PEG or POZ can be conjugated directly to the lipid or may be linked to the lipid via a linker moiety. Any linker moiety suitable for coupling the PEG or the POZ to a lipid can be used including, e.g., non-ester-containing linker moieties and ester-containing linker moieties. In certain preferred embodiments, non-ester-containing linker moieties, such as amides or carbamates, are used.

The term "substituted" means substitution with specified groups other than hydrogen, or with one or more groups, moieties, or radicals which can be the same or different, with each, for example, being independently selected.

By "nucleotide" as used herein is as recognized in the art to include natural bases (standard), and modified bases well known in the art. Such bases are generally located at the 1' position of a nucleotide sugar moiety. Nucleotides generally comprise a base, sugar, and a phosphate group. The nucleotides can be unmodified or modified at the sugar, phosphate, and/or base moiety, (also referred to interchangeably as nucleotide analogs, modified nucleotides, non-natural nucleotides, non-standard nucleotides and other. Some of the non-limiting examples of base modifications that can be introduced into nucleic acid molecules include: inosine, purine, pyridin-4-one, pyridin-2-one, phenyl, pseudouracil, 2,4,6-trimethoxy benzene, 3-methyl uracil, dihydrouridine, naphthyl, aminophenyl, 5-alkylcytidines (e.g., 5-methylcytidine), 5-alkyluridines (e.g., ribothymidine), 5-halouridine (e.g., 5-bromouridine) or 6-azapyrimidines or 6-alkylpyrimidines (e.g., 6-methyluridine), propyne, and others. By "modified bases" in this aspect is meant nucleotide bases other than adenine, guanine, cytosine, and uracil at 1' position or their equivalents.

"Nucleic acid" refers to deoxyribonucleotides or ribonucleotides and polymers thereof in single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2'-O-methyl ribonucleotides, peptide-nucleic acids (PNAs).

By "RNA" is meant a molecule comprising at least one ribonucleotide residue. By "ribonucleotide" is meant a nucleotide with a hydroxyl group at the 2' position of a β-D-ribo-furanose moiety, or an acyclic analog where the C2'-C3' bond of 3-D-ribo-furanose is absent (UNA). The terms include double-stranded RNA, single-stranded RNA, isolated RNA such as partially purified RNA, essentially pure RNA, synthetic RNA, recombinantly produced RNA, as well as altered RNA that differs from naturally occurring RNA by the addition, deletion, substitution, and/or alteration of one or more nucleotides. Such alterations can include addition of non-nucleotide material, such as to the end(s) of an interfering RNA or internally, for example at one or more nucleotides of the RNA. Nucleotides in the RNA molecules of the instant invention can also comprise non-standard nucleotides, such as non-naturally occurring nucleotides or chemically synthesized nucleotides or deoxynucleotides. These altered RNAs can be referred to as analogs or analogs of naturally-occurring RNA. As used herein, the terms "ribonucleic acid" and "RNA" refer to a molecule containing at least one ribonucleotide residue, including siRNA, antisense RNA, single stranded RNA, microRNA, mRNA, noncoding RNA, and multivalent RNA.

As used herein complementary nucleotide bases are a pair of nucleotide bases that form hydrogen bonds with each other. Adenine (A) pairs with thymine (T) or with uracil (U) in RNA, and guanine (G) pairs with cytosine (C). Complementary segments or strands of nucleic acid that hybridize (join by hydrogen bonding) with each other. By "complementary" is meant that a nucleic acid can form hydrogen bond(s) with another nucleic acid sequence either by traditional Watson-Crick or by other non-traditional modes of binding.

By "antisense nucleic acid", it is meant a non-enzymatic nucleic acid molecule that binds to target RNA by means of RNA-RNA or RNA-DNA or RNA-PNA (protein nucleic acid) interactions and alters the activity of the target RNA. Typically, antisense molecules are complementary to a target sequence along a single contiguous sequence of the antisense molecule. However, in certain embodiments, an antisense molecule can bind to substrate such that the substrate molecule forms a loop, and/or an antisense molecule can bind such that the antisense molecule forms a loop. Thus, the antisense molecule can be complementary to two (or even more) non-contiguous substrate sequences or two (or even more) non-contiguous sequence portions of an antisense molecule can be complementary to a target sequence or both. In addition, antisense DNA can be used to target RNA by means of DNA-RNA interactions, thereby activating RNase H, which digests the target RNA in the duplex. The antisense oligonucleotides can comprise one or more RNAse H activating region, which is capable of activating RNAse H cleavage of a target RNA. Antisense DNA can be synthesized chemically or expressed via the use of a single stranded DNA expression vector or equivalent thereof.

"Antisense RNA" is an RNA strand having a sequence complementary to a target gene mRNA, that can induce RNAi by binding to the target gene mRNA. "Antisense RNA" is an RNA strand having a sequence complementary to a target gene mRNA, and thought to induce RNAi by binding to the target gene mRNA. "Sense RNA" has a sequence complementary to the antisense RNA, and annealed to its complementary antisense RNA to form iNA. These antisense and sense RNAs have been conventionally synthesized with an RNA synthesizer.

MicroRNAs (miRNA) are single-stranded RNA molecules of 21-23 nucleotides in length, which regulate gene expression miRNAs are encoded by genes that are transcribed from DNA but not translated into protein (non-coding RNA); instead they are processed from primary transcripts known as pri-miRNA to short stem-loop structures called pre-miRNA and finally to functional miRNA. Mature miRNA molecules are partially complementary to one or more messenger RNA (mRNA) molecules, and their main function is to downregulate gene expression As used herein the term "small interfering RNA (siRNA) ", sometimes known as short interfering RNA or silencing RNA, is used to refer to a class of double-stranded RNA molecules, 16-40 nucleotides in length, that play a variety of roles in biology. Most notably, siRNA is involved in the RNA interference (RNAi) pathway, where it interferes with the expression of a specific gene. In addition to their role in the RNAi pathway, siRNAs also act in RNAi-related pathways, e.g., as an antiviral mechanism or in shaping the chromatin structure of a genome; the complexity of these pathways is only now being elucidated.

As used herein, the term RNAi refers to an RNA-dependent gene silencing process that is controlled by the RNA-induced silencing complex (RISC) and is initiated by short double-stranded RNA molecules in a cell, where they interact with the catalytic RISC component argonaute. When the double-stranded RNA or RNA-like iNA or siRNA is exogenous (coming from infection by a virus with an RNA genome or from transfected iNA or siRNA), the RNA or iNA is imported directly into the cytoplasm and cleaved to short fragments by the enzyme dicer. The initiating dsRNA can also be endogenous (originating in the cell), as in pre-microRNAs expressed from RNA-coding genes in the genome. The primary transcripts from such genes are first processed to form the characteristic stem-loop structure of pre-miRNA in the nucleus, then exported to the cytoplasm to be cleaved by dicer. Thus, the two dsRNA pathways, exogenous and endogenous, converge at the RISC complex. The active components of an RNA-induced silencing complex (RISC) are endonucleases called argonaute proteins, which cleave the target mRNA strand complementary to their bound siRNA or iNA. As the fragments produced by dicer are double-stranded, they could each in theory produce a functional siRNA or iNA. However, only one of the two strands, which is known as the guide strand, binds the argonaute protein and directs gene silencing. The other anti-guide strand or passenger strand is degraded during RISC activation.

Also within the scope of the present disclosure are polymorphs of the compounds of this disclosure (i.e., polymorphs of the compounds of formula I are within the scope of this disclosure).

All stereoisomers (for example, geometric isomers, optical isomers, and the like) of the present compounds (including those of the salts, solvates, and prodrugs of the compounds as well as the salts and solvates of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this disclosure. Individual stereoisomers of the compounds of this disclosure may, for example, be substantially free of other isomers, or may be admixed, for example, as racemates or with all other, or other selected, stereoisomers. The chiral centers of the compounds herein can have the S or R configuration. The use of the terms "salt", "solvate", and the like, is intended to equally apply to the salt and solvate of enantiomers, stereoisomers, rotamers, tautomers, racemates, or prodrugs of the disclosed compounds.

Classes of compounds that can be used as the chemotherapeutic agent (antineoplastic agent) include: alkylating agents, antimetabolites, natural products and their derivatives, hormones and steroids (including synthetic analogs), and synthetics. Examples of compounds within these classes are given below.

Process of Synthesis

Another aspect of the description is a process of making a multiligand compound shown formula 45

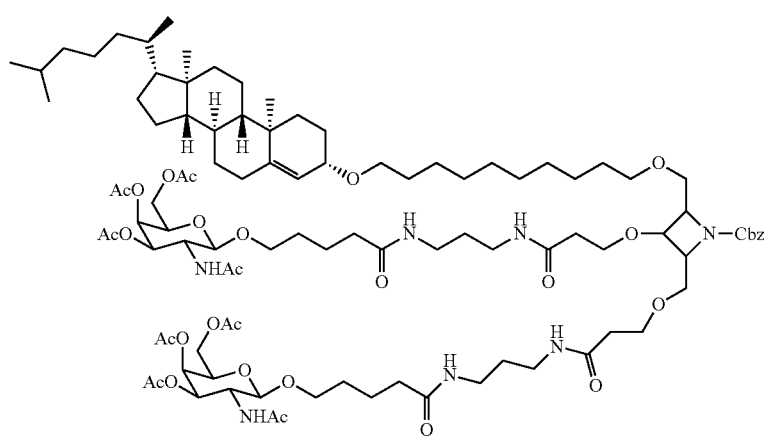

45 the process comprising the steps of
i. reacting aminotriol compound

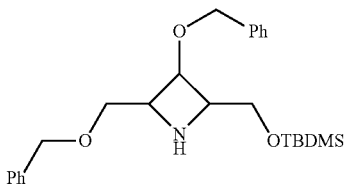 [SMILES: CC(C)(C)[Si](C)(C)OCC1NC(COCc2ccccc2)C1OCc1ccccc1]

5 with a lipophile 42

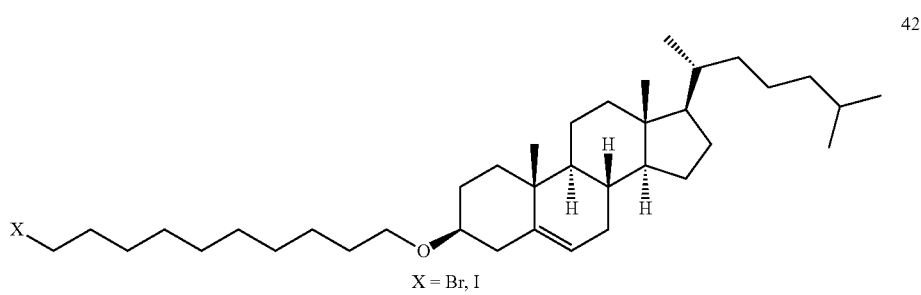

42

X = Br, I ii. removing hydroxyl protecting groups from the product of step i;
iii. reacting the product of step ii with (CHCH)COO-t-butyl in NaOH;
iv. adding an amino protecting group to the product of step iii;
v. reacting the product of step iv with BocN(CH₂)₃NH₂ using EDC and HOBT;
vi. reacting the product of step v with GalNAc acid

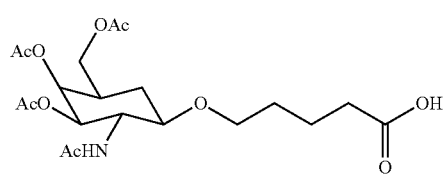 [SMILES: CC(=O)NC1C(OCCCCC(=O)O)CC(COC(C)=O)C(OC(C)=O)C1OC(C)=O]

using EDC, HOBT, and N,N-diisopropylethylamine.

The starting material for the process preferably is an aminotriol having the structure of formula 1, 5, or 9.

-continued

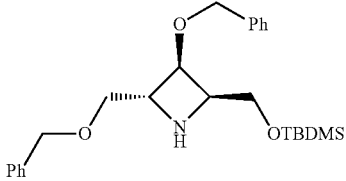

5

9

Another aspect of the description is process of making a multiligand compound shown formula 53

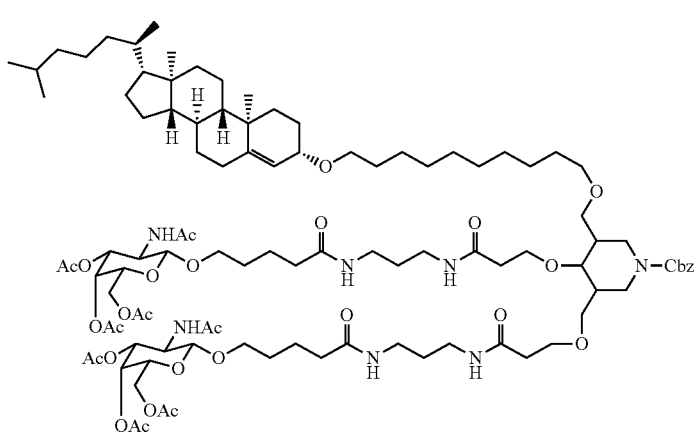

53 the process comprising the steps of
i. reacting aminotriol compound

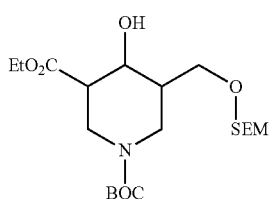 [SMILES: CCOC(=O)C1CN(C(=O)OC(C)(C)C)CC(COCOCC[Si](C)(C)C)C1O]

20 with n-Bu4NF,
ii. reacting the product of step i with CH$_3$C(OCH$_3$)$_2$CH$_3$ and p-toluenesulfonic acid,
iii. reacting the product of step ii with LiBH$_4$,
iv. reacting the product of step iii with a lipophile 42, v. removing hydroxyl protecting groups from the product of step iv;

vi. reacting the product of step v with (CHCH)COO-t-butyl in NaOH;

vii. adding an amino protecting group to the product of vi;

viii. reacting the product of step viii with BocN(CH$_2$)$_3$NH$_2$ using EDC and HOBT;

ix. reacting the product of step ix with GalNAc acid

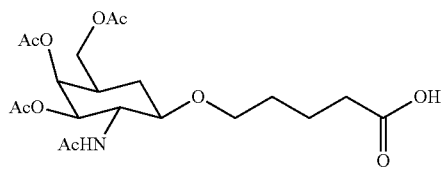 [SMILES: CC(=O)NC1C(OCCCCC(=O)O)CC(COC(C)=O)C(OC(C)=O)C1OC(C)=O]

using EDC, HOBT, and N,N-diisopropylethylamine.

The process preferably starts with an aminotriol compound having the structure of formula 13, 19, or 30

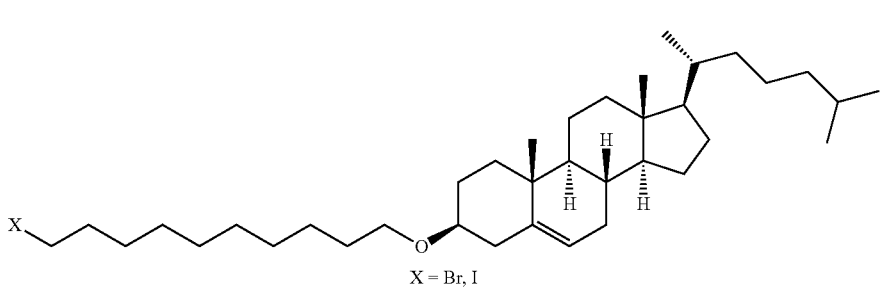

42

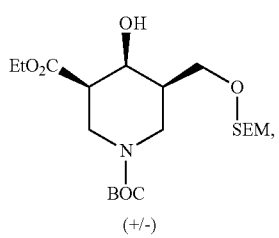

13

(+/−)

31
-continued
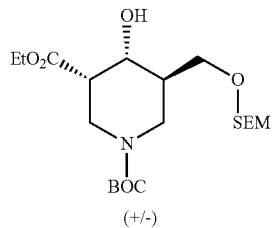
(+/-)
32
-continued
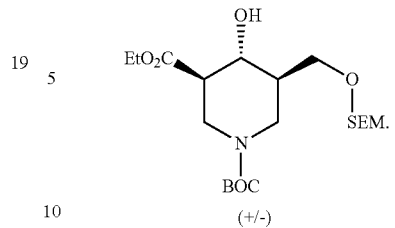
(+/-)
Another aspect of the description is process of making a multiligand compound shown formula 45,
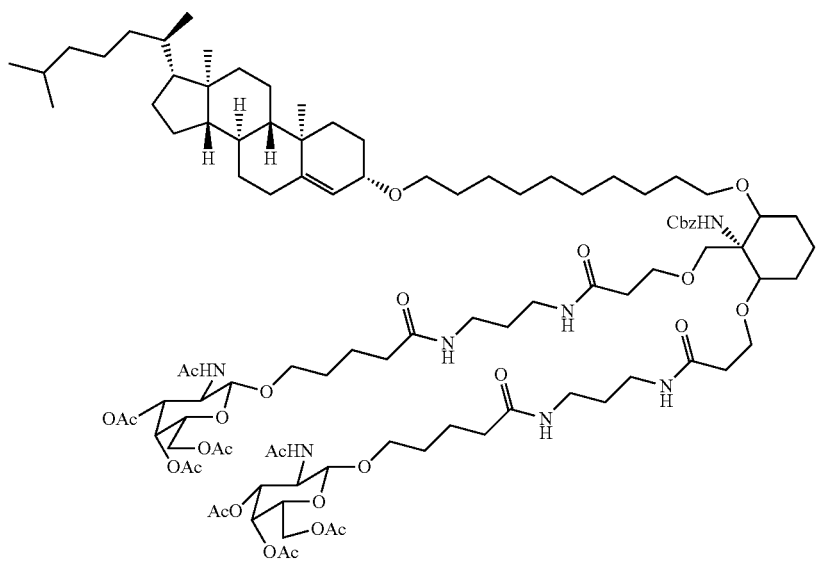

the process comprising the steps of
  i. reacting aminotriol compound having formula 38

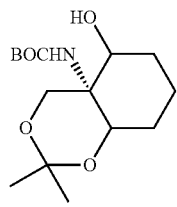

with a lipophile 42,

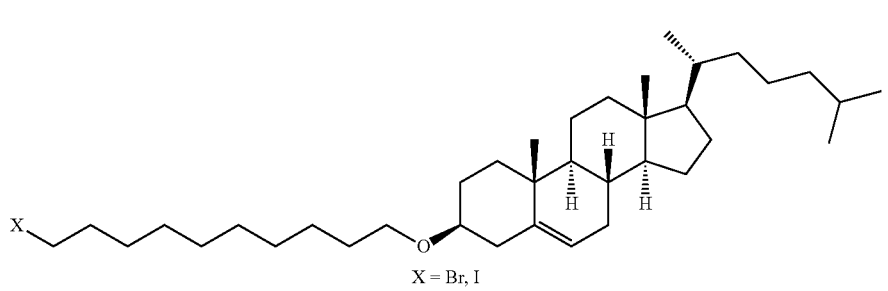

ii. removing hydroxyl protecting groups from the product of step i;
iii. reacting the product of step ii with (CHCH)COO-t-butyl in NaOH;
iv. adding an amino protecting group to the product of step iii;
v. reacting the product of step iv with BocN(CH$_2$)$_3$NH$_2$ using EDC and HOBT;
vi. reacting the product of step v with GalNAc acid

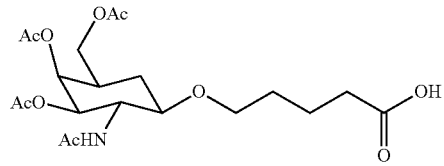 [SMILES: CC(=O)NC1C(OCCCCC(=O)O)CC(COC(C)=O)C(OC(C)=O)C1OC(C)=O]

using EDC, HOBT, and N,N-diisopropylethylamine.

Compositions and Formulations for Administration

Another aspect of the description herein is a pharmaceutical composition comprising a compound consisting of an aminotriol of formula I, II, or III,

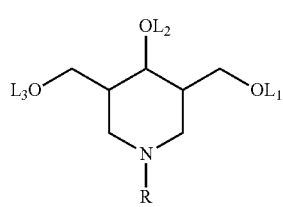

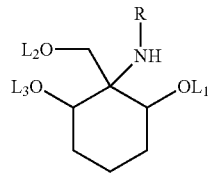

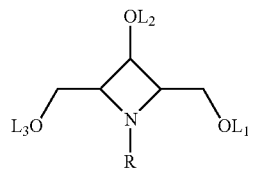

wherein R comprises a therapeutic molecule, and L$_1$, L$_2$, and L$_3$ independently for each occurrence comprise a ligand selected from the group consisting of a carbohydrate, a polypeptide, or a lipophile. The pharmaceutical composition may further comprise a pharmaceutically acceptable counterion or a pharmaceutically acceptable excipient. Preferably, the therapeutic molecule is an RNA, more preferably a double-stranded siRNA. The double-stranded siRNA may comprise a UNA. Preferably the L$_2$ and L$_3$ ligand are a carbohydrate, most preferably, 1'-O—(N-acetyl-D-galactosylamine) or 1'-O-(D-galactose).

The compositions of description herein may be administered by various routes, for example, to effect systemic delivery via intravenous, parenteral, intraperitoneal, or topical routes. In some embodiments, a siRNA may be delivered intracellularly, for example, in cells of a target tissue such as lung or liver, or in inflamed tissues. In some embodiments, this disclosure provides a method for delivery of siRNA in vivo. A nucleic acid-lipid composition may be administered intravenously, subcutaneously, or intraperitoneally to a subject. In some embodiments, the disclosure provides methods for in vivo delivery of interfering RNA to the lung of a mammalian subject.

The compositions and methods of the disclosure may be administered to subjects by a variety of mucosal administration modes, including by oral, rectal, vaginal, intranasal, intrapulmonary, or transdermal or dermal delivery, or by topical delivery to the eyes, ears, skin, or other mucosal surfaces. In some aspects of this disclosure, the mucosal tissue layer includes an epithelial cell layer. The epithelial cell can be pulmonary, tracheal, bronchial, alveolar, nasal, buccal, epidermal, or gastrointestinal. Compositions of this disclosure can be administered using conventional actuators such as mechanical spray devices, as well as pressurized, electrically activated, or other types of actuators. The compositions preferably are administered subcutaneously by injection.

In some embodiments, this disclosure is a pharmaceutical product which includes a solution containing a composition of this disclosure and an actuator for a pulmonary, mucosal, or intranasal spray or aerosol.

A dosage form of the composition of this disclosure can be liquid, in the form of droplets or an emulsion, or in the form of an aerosol.

A dosage form of the composition of this disclosure can be solid, which can be reconstituted in a liquid prior to administration. The solid can be administered as a powder. The solid can be in the form of a capsule, tablet, or gel.

The biologically active agent may be dispersed in a base or vehicle, which may comprise a hydrophilic compound having a capacity to disperse the active agent and any desired additives. The base may be selected from a wide range of suitable carriers, including but not limited to, copolymers of polycarboxylic acids or salts thereof, carboxylic anhydrides (e.g., maleic anhydride) with other monomers (e.g., methyl(meth)acrylate, acrylic acid, etc.), hydrophilic vinyl polymers such as polyvinyl acetate, polyvinyl alcohol, polyvinylpyrrolidone, cellulose derivatives such as hydroxymethylcellulose, hydroxypropylcellulose, etc., and natural polymers such as chitosan, collagen, sodium alginate, gelatin, hyaluronic acid, and nontoxic metal salts thereof. Often, a biodegradable polymer is selected as a base or carrier, for example, polylactic acid, poly(lactic acid-glycolic acid) copolymer, polyhydroxybutyric acid, poly (hydroxybutyric acid-glycolic acid) copolymer, and mixtures thereof. Alternatively or additionally, synthetic fatty acid esters such as polyglycerin fatty acid esters, sucrose fatty acid esters, etc., can be employed as carriers. Hydrophilic polymers and other carriers can be used alone or in combination, and enhanced structural integrity can be imparted to the carrier by partial crystallization, ionic bonding, crosslinking, and the like. The carrier can be provided in a variety of forms, including fluid or viscous solutions, gels, pastes, powders, microspheres, and films for direct application to the nasal mucosa. The use of a selected carrier in this context may result in promotion of absorption of the biologically active agent.

Formulations for mucosal, nasal, or pulmonary delivery may contain a hydrophilic low molecular weight compound as a base or excipient. Such hydrophilic low molecular weight compounds provide a passage medium through which a water-soluble active agent, such as a physiologically active peptide or protein, may diffuse through the base to the body surface where the active agent is absorbed. The hydrophilic low molecular weight compound optionally absorbs moisture from the mucosa or the administration atmosphere and dissolves the water-soluble active peptide. The molecular weight of the hydrophilic low molecular weight compound is 3,000-10,000 Daltons. Examples of hydrophilic low molecular weight compounds include polyol compounds, such as oligo-, di- and monosaccharides including sucrose, mannitol, lactose, L-arabinose, D-erythrose, D-ribose, D-xylose, D-mannose, D-galactose, lactulose, cellobiose, gentiobiose, glycerin, polyethylene glycol, and mixtures thereof. Further examples of hydrophilic low molecular weight compounds include N-methylpyrrolidone, alcohols (e.g., oligovinyl alcohol, ethanol, ethylene glycol, propylene glycol, etc.), and mixtures thereof.

The compositions of this disclosure may alternatively contain as pharmaceutically acceptable carriers substances as required to approximate physiological conditions, such as pH adjusting and buffering agents, tonicity adjusting agents, and wetting agents, for example, sodium acetate, sodium lactate, sodium chloride, potassium chloride, calcium chloride, sorbitan monolaurate, triethanolamine oleate, and mixtures thereof. For solid compositions, conventional nontoxic pharmaceutically acceptable carriers can be used which include, for example, pharmaceutical grades of mannitol, lactose, starch, magnesium stearate, sodium saccharin, talcum, cellulose, glucose, sucrose, magnesium carbonate, and the like.

In certain embodiments of the description herein, the biologically active agent may be administered in a time release formulation, for example in a composition which includes a slow release polymer. The active agent can be prepared with carriers that will protect against rapid release, for example a controlled release vehicle such as a polymer, microencapsulated delivery system, or bioadhesive gel. Prolonged delivery of the active agent, in various compositions of the disclosure can be brought about by including in the composition agents that delay absorption, for example, aluminum monosterate hydrogels and gelatin.

Another aspect of the description herein is a method of treating a disease comprising administering a therapeutically effective amount of a pharmaceutical composition comprising a compound consisting of an aminotriol of formula I, II, or III,

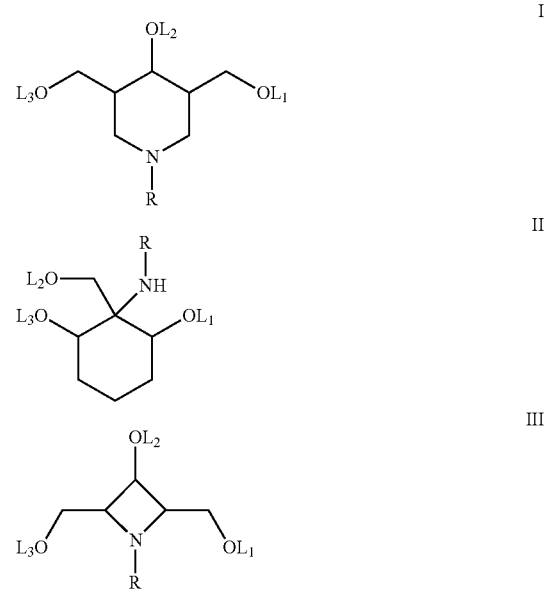

wherein R comprises a therapeutic molecule, and $L_1$, $L_2$, and $L_3$ independently for each occurrence comprise a ligand selected from the group consisting of a carbohydrate, a polypeptide, or a lipophile. The compound may comprise an RNA that knocks down expression of a target gene is selected from the group consisting of Factor VII, Eg5, PCSK9, TPX2, apoB, SAA, TTR, RSV, PDGF beta gene, Erb-B gene, Src gene, CRK gene, GRB2 gene, RAS gene, MEKK gene, JNK gene, RAF gene, Erk1/2 gene, PCNA (p21) gene, MYB gene, JUN gene, FOS gene, BCL-2 gene, Cyclin D gene, VEGF gene, EGFR gene, Cyclin A gene, Cyclin E gene, WNT-1 gene, beta-catenin gene, c-MET gene, PKC gene, NFKB gene, STAT3 gene, survivin gene, Her2/Neu gene, topoisomerase I gene, topoisomerase II alpha gene, mutations in the p73 gene, mutations in the p21(WAF1/CIP1) gene, mutations in the p27(KIP1) gene, mutations in the PPM1D gene, mutations in the RAS gene, mutations in the caveolin I gene, mutations in the MIB I gene, mutations in the MTAI gene, mutations in the M68 gene, mutations in tumor suppressor genes, and mutations in the p53 tumor suppressor gene. The pharmaceutical composition preferably is administered subcutaneously.

While this disclosure has been described in relation to certain embodiments, and many details have been set forth for purposes of illustration, it will be apparent to those skilled in the art that this disclosure includes additional embodiments, and that some of the details described herein may be varied considerably without departing from this disclosure. This disclosure includes such additional embodiments, modifications, and equivalents. In particular, this disclosure includes any combination of the features, terms, or elements of the various illustrative components and examples.

EXAMPLES

The aminotriols described herein provide a means for selective steroid/linker attachment. The fully deprotected compounds of formulas Ia, Ib, Ic, II, IIIa, IIIb, and IIIc, above, are readily synthesized by the methods described in equations (1)-(7) shown in FIGS. 1-7. Compounds 1, 5, 9, 13, 19, and 30 afford either differentiated protecting functions with a single —OH moiety free for reaction, or the opportunity to manipulate protecting functions so as to allow a single —OH to be free for reaction. This provides the opportunity to selectively introduce the $L_1$, $L_2$, and $L_3$ moieties as described in equations (1)-(7). $L_1$ is a cholesteryl substituent, and $L_2$ and $L_3$ are GalNAc.

Example 1

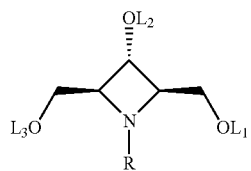

IIIa

The aminotriol of formula IIIa is synthesized by the reactions according to the method shown in equation (1) in FIG. 1.

Figure 8:
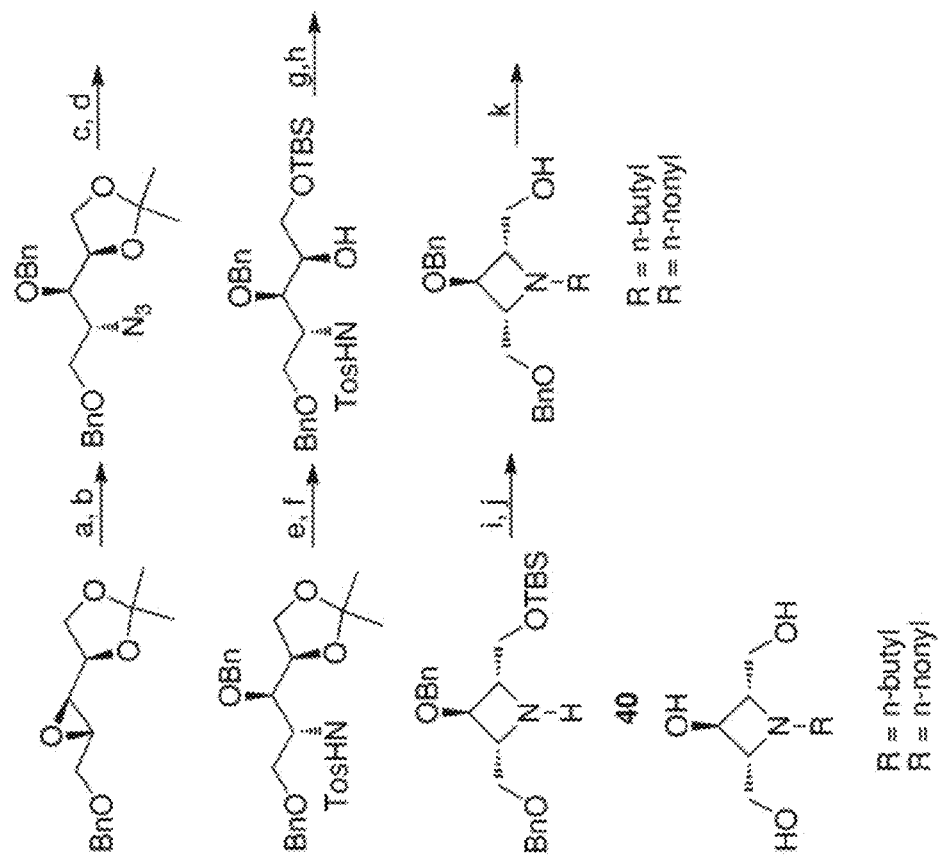
FIG. 8 shows the synthesis of compound 1.

The starting material for equation (1), compound 1, is made according to the method shown in FIG. 8 as described in Lee, 2012, *J Org Chem*, 77:3082-98, hereby incorporated by reference. Starting with known epoxyacetonide, the process furnished the (2R,3S,4S)-3-hydroxyazetidine. Reagents and conditions are as follows: (a) $NaN_3$, $NH_4Cl$, 2-methoxyethanol, water 9:1, reflux; (b) NaH, benzyl bromide, TBAI, THF, room temperature, 1 hour; (c) $LiAlH_4$, THF; (d) tosyl chloride, triethylamine, $CH_2Cl_2$, room temperature; (e) 2N HCl:methanol, 40° C.; (f) TBSCl, triethylamine, DMAP, $CH_2Cl_2$; (g) $PPh_3$, DIAD, $CH_2Cl_2$, room temperature; (h) Na, naphthalene, DME, −60° C.; (i) aldehyde (butyraldehyde or nonyl aldehyde), sodium triacetoxyborohydride, $ClCH_2CH_2Cl$, room temperature; (j) TBAF, THF, room temperature; (k) $PdCl_2$, $H_2$, methanol.

Example 2

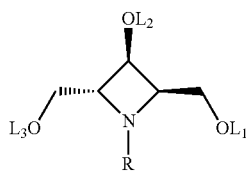

IIIb

Figure 2:
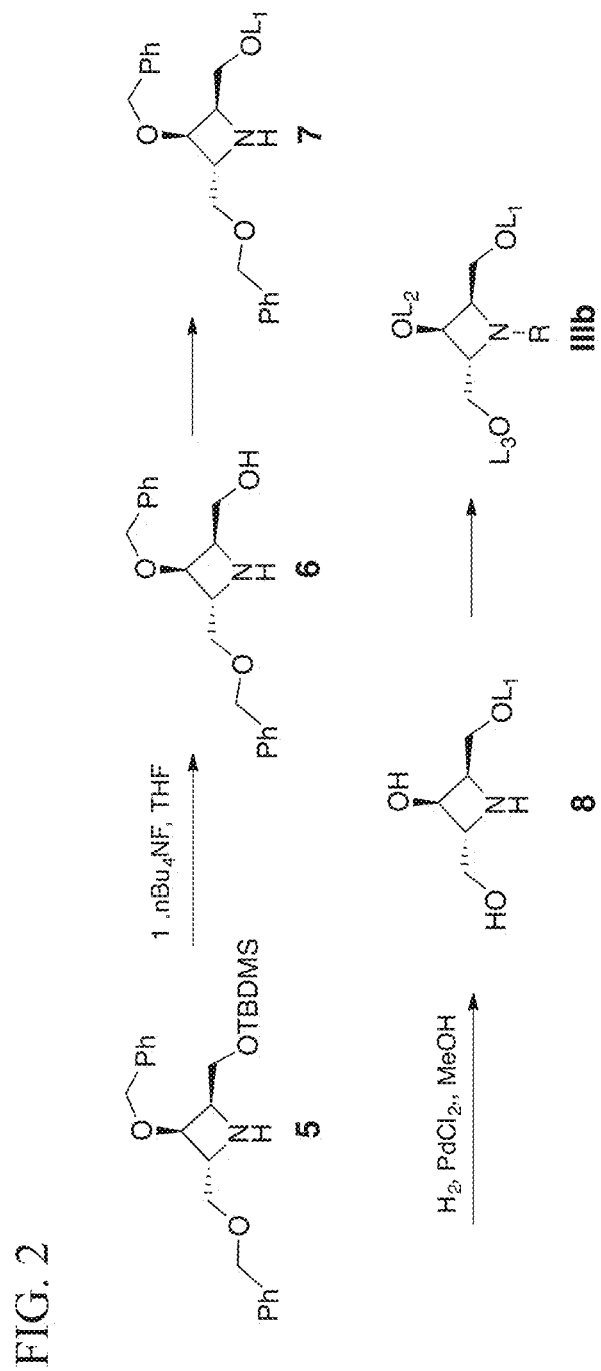
FIG. 2 shows equation (2) for the synthesis of the aminotriol of formula IIIb.

The aminotriol of formula IIIb is synthesized according to the method shown in equation (2) in FIG. 2.

Figure 9:
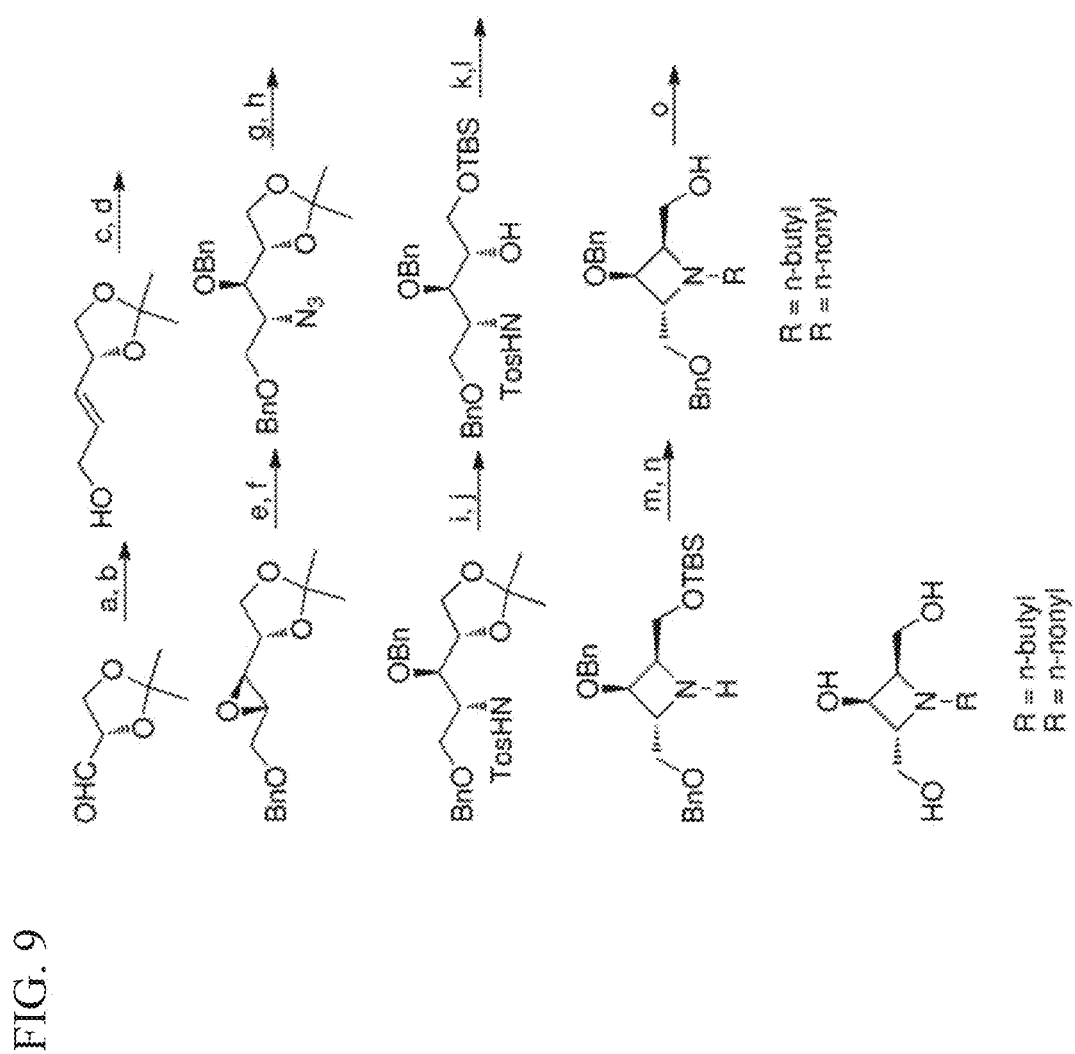
FIG. 9 shows the synthesis of compound 5.

The starting material for equation (2), compound 5, is made according to the method shown in FIG. 9 as described in Lee. The synthesis of the four-membered imino sugar is started by subjecting $L$-glyceraldehyde acetonide to a Wittig reaction (a) with carbethoxymethylene-triphenylphosphorane in benzene, with reflux, followed by (b) diisobutylaluminium hydride (DIBAL-H) reduction in $CH_2Cl_2$ at −78° C. to 0° C., to furnish the allylic alcohol. Sharpless epoxidation (c) using cumene hydroperoxide, (+)-diisopropyl L-tartrate (DIPT), titanium tetraisopropoxide ($Ti(OiPr)_4$), 3 Å molecular sieves, $CH_2Cl_2$, −40° C., and protection of the hydroxyl group by reaction (d) with NaH, benzyl bromide, tetrabutylammonium iodide (TBAI), in tetrahydrofuran (THF) at room temperature for 1 hour provides epoxide. The epoxide is opened (e) with sodium azide with $NH_4Cl_2$ in methoxyethanol:water 9:1, under reflux, and the secondary hydroxyl group is benzylated (f) by NaH, benzyl bromide, TBAI, THF, at room temperature for 1 hour to yield a benzyl ether. The azide group is reduced (g) with $LiAlH_4$ in THF, and the resulting amino group is reacted (h) with tosyl chloride in triethylamine and $CH_2Cl_2$ to form a tosylate. The acetonide protecting group of intermediate is removed (i) in 2N HCl:methanol, at 40° C., and the primary alcohol is converted (j) in t-butyldimethylsilyl chloride (TBSCl), triethylamine, 4-dimethylaminopyridine (DMAP), $CH_2Cl_2$ to silyl ether 33. Ring closure to the four-membered ring is accomplished by a Mitsunobu reaction (k) triphenyl-phosphine, diisopropyl azodicarboxylate (DIAD), $CH_2Cl_2$, room temperature, which is followed by reductive removal of the N-tosyl group (1) Na, naphthalene, dimethoxyethane (DME) at −60° C. to furnish an azetidine. The azetidine is subjected to reductive amination with butyraldehyde and nonyl aldehyde (m) in sodium triacetoxyborohydride, $ClCH_2CH_2Cl$ at room temperature, followed by desilylation (n) tetra-n-butylammonium fluoride (TBAF), THF, at room temperature to afford an intermediate. Hydrogenolysis of the benzyl protecting groups (o) by $PdCl_2$ and hydrogen in methanol yielded the targeted four-membered (2R,4R)-3-hydroxyazetidine.

Example 3

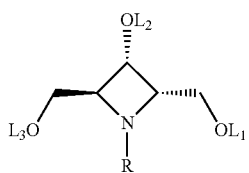

IIIc

Figure 3:
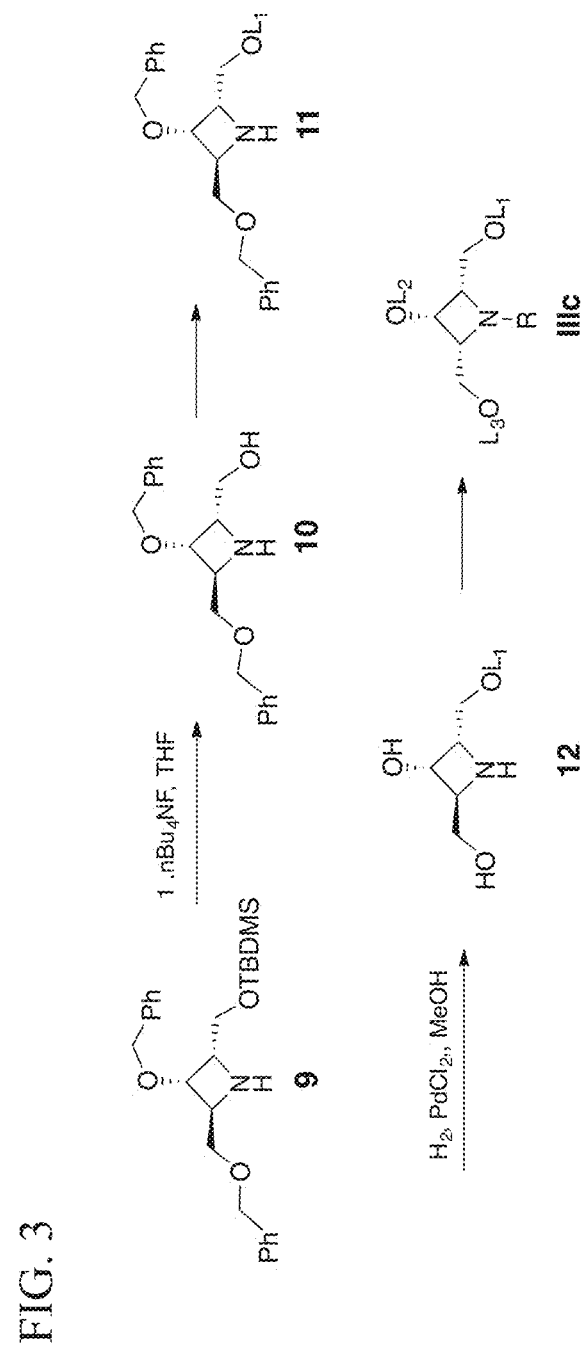
FIG. 3 shows equation (3) for the synthesis of the aminotriol of formula IIIc.

The aminotriol of formula IIIc is synthesized according to the method shown in equation (3) of FIG. 3.

Figure 10:
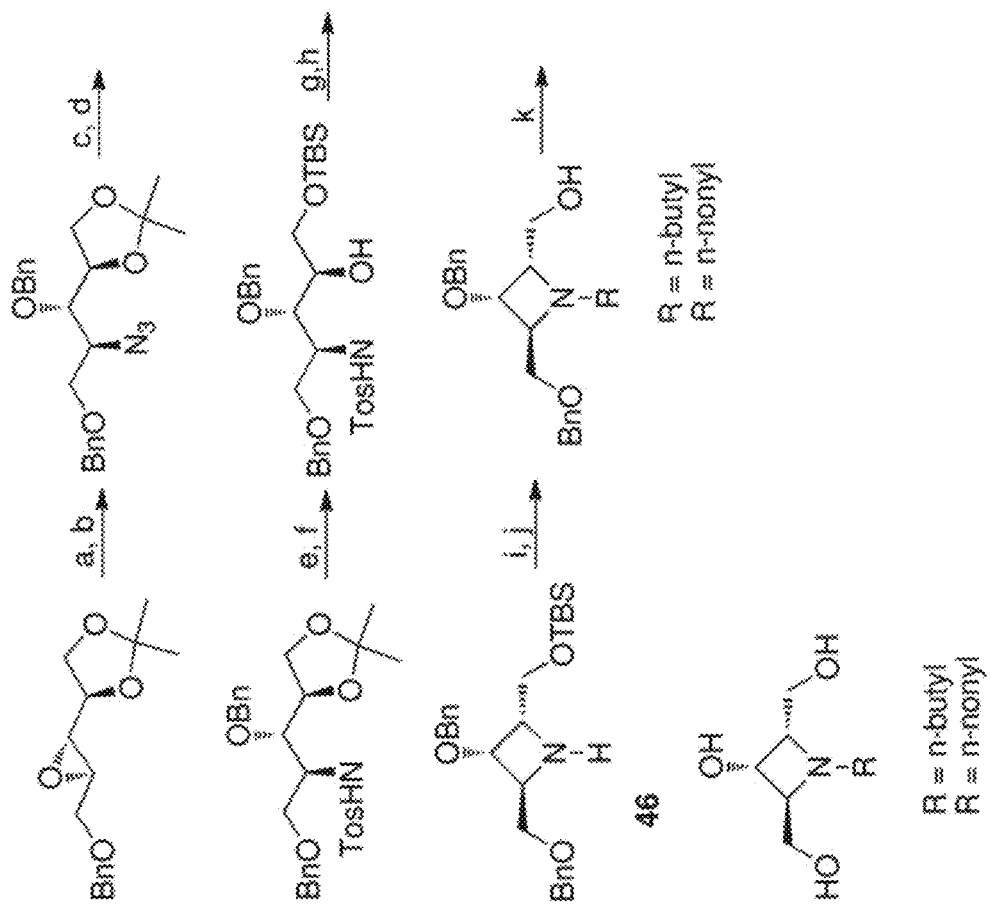
FIG. 10 shows the synthesis of compound 9.

The starting material for equation (3), compound 9, is made according to the method shown in FIG. 10 as described in Lee. Reagents and conditions: (a) $NaN_3$, $NH_4Cl$, 2-methoxyethanol, water 9:1, reflux; (b) NaH, benzyl bromide, TBAI, THF, room temperature, 1 hour; (c) $LiAlH_4$, THF; (d) tosyl chloride, triethylamine, $CH_2Cl_2$, room temperature; (e) 2N HCl:methanol, 40° C.; (f) TBSCl, triethylamine, DMAP, $CH_2Cl_2$; (g) $PPh_3$, DIAD, $CH_2Cl_2$, room temperature; (h) Na, naphthalene, DME, −60° C.; (i) aldehyde (butyraldehyde or nonyl aldehyde), sodium triacetoxyborohydride, $ClCH_2CH_2Cl$, room temperature; (j) TBAF, THF, room temperature; (k) $PdCl_2$, hydrogen, methanol.

Example 4

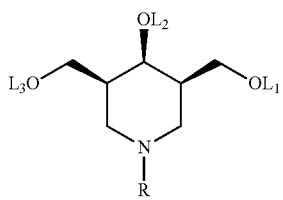

Ia

Figure 4:
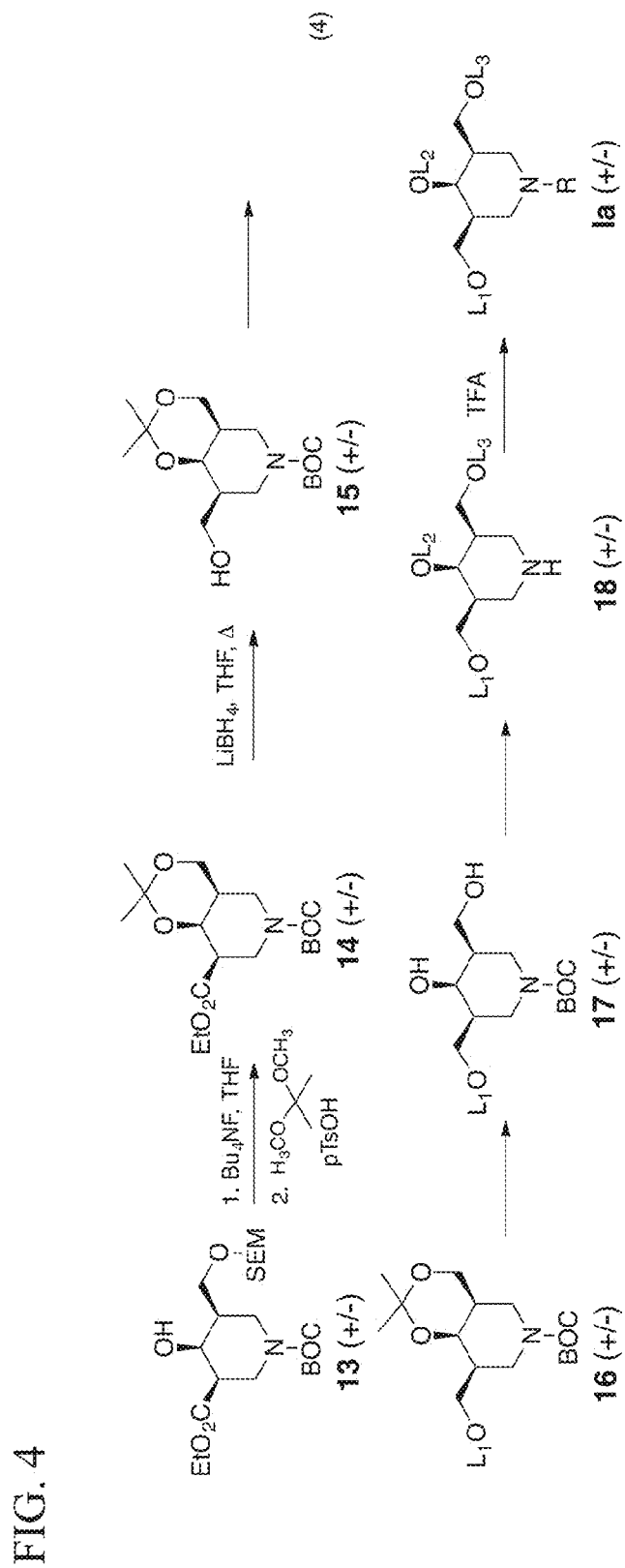
FIG. 4 shows equation (4) for the synthesis of the aminotriol of formula Ia.

The aminotriol of formula Ia is synthesized according to the method equation (4) shown in FIG. 4.

Figure 11:
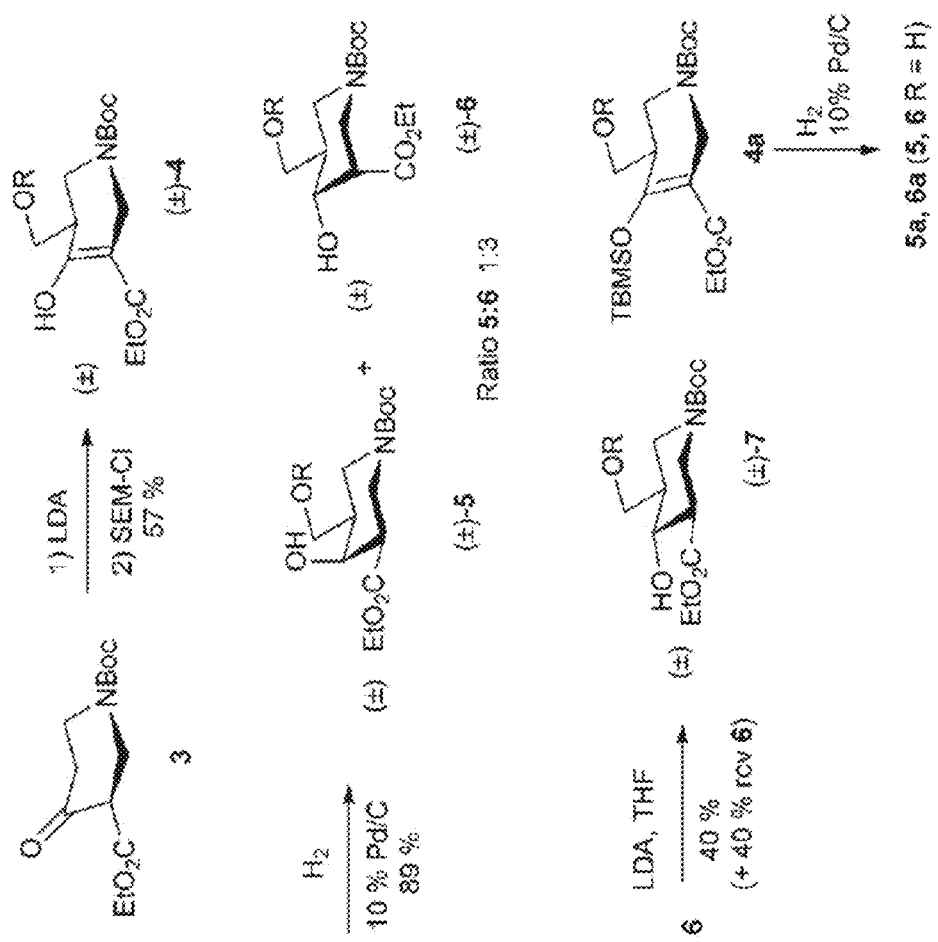
FIG. 11 shows the synthesis of intermediates 5-7.
Figure 12:
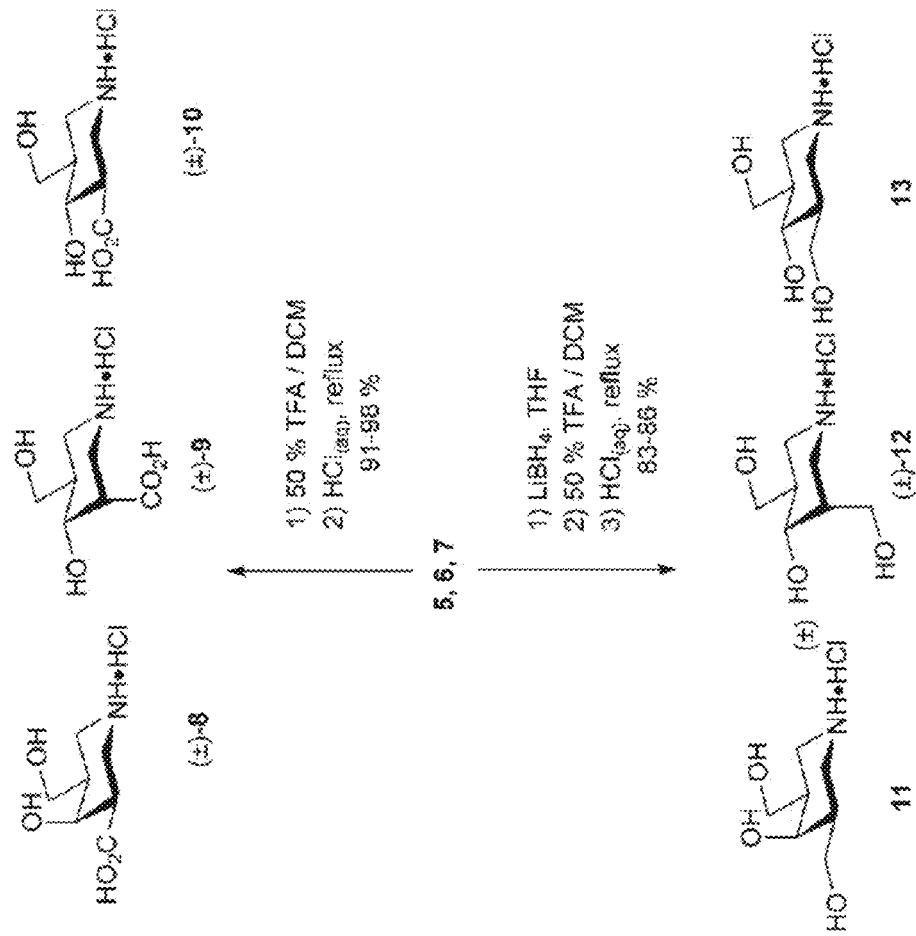
FIG. 12 shows the product of hydrolysis of intermediates 5-7.

The starting material for equation (4), compound 13, is prepared as described in Lohse, 2000, *J Chem Soc Perkin Trans, I*:659-65, hereby incorporated by reference, as shown in FIGS. 11 and 12. Synthesis of the three key intermediates 5-7 of FIG. 12 is according to the method shown in FIG. 11. The starting material for the synthesis is the commercial available ethyl 4-oxopiperidine-3-carboxylate hydrochloride protected with di-tert-butyl pyrocarbonate. Treatment with lithium diisopropylamide (LDA) generates the dianion which can be selectively alkylated with 2-(trimethylsilyl)ethoxymethyl chloride (SEM-C1) in the more reactive 5-position. Complete removal of the protecting groups gives compounds by first treating the products of the reaction with 50% TFA in $CH_2Cl_2$ followed by aqueous hydrolysis in 4 M hydrochloric acid, according to the method shown in FIG. 12. A second series of derivatives are made by first reducing the ester function with $LiBH_4$ followed by removal of protecting groups. The three bishydroxymethyl compounds also served as proof for the correct assignment of the configuration of the key intermediates.

Example 5

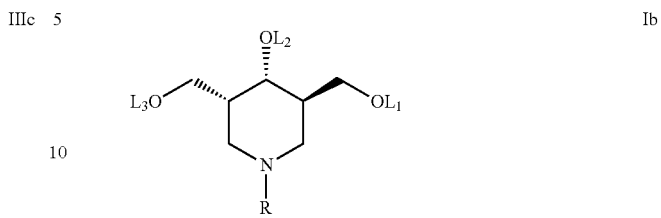

Ib

Figure 5:
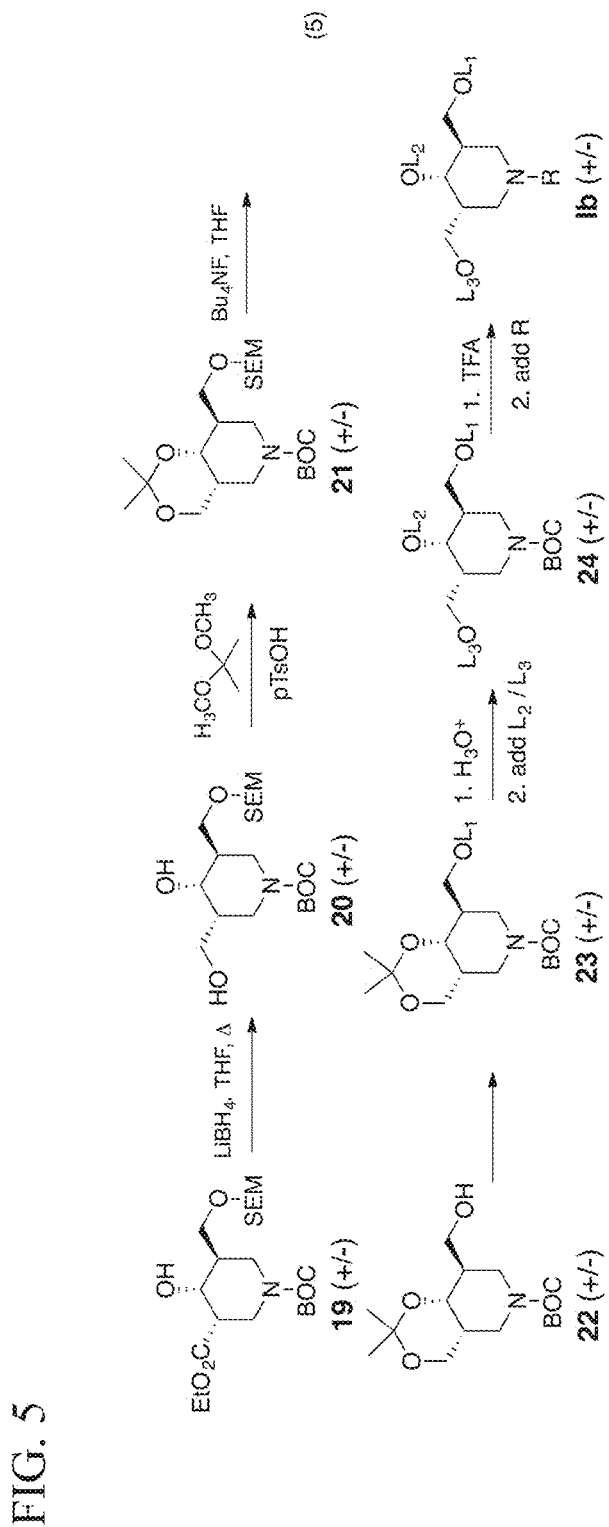
FIG. 5 shows equation (5) for the synthesis of the aminotriol of formula Ib.
Figure 6:
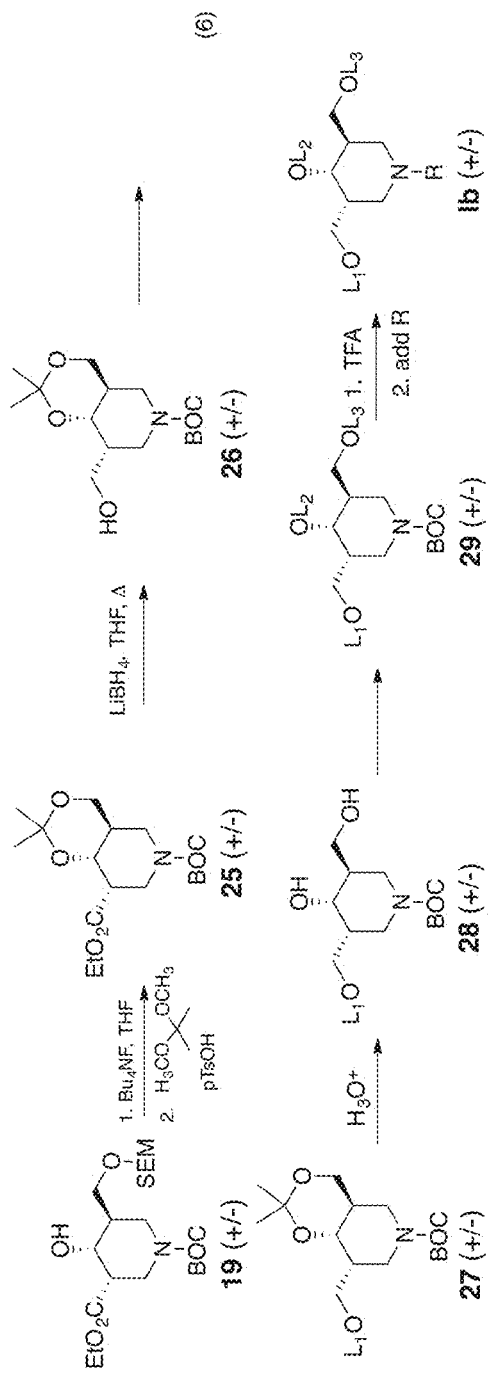
FIG. 6 shows equation (6) for the synthesis of the aminotriol of formula Ib.

The aminotriol of each isomer of formula Ib is synthesized according to the methods of equations (5) and (6), as shown in FIGS. 5 and 6, respectively. The starting material of equations (5) and (6), compound 19, is prepared as described in Example 4 using the methods of Lohse.

Example 6

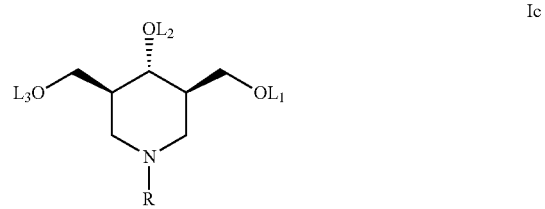

Ic

Figure 7:
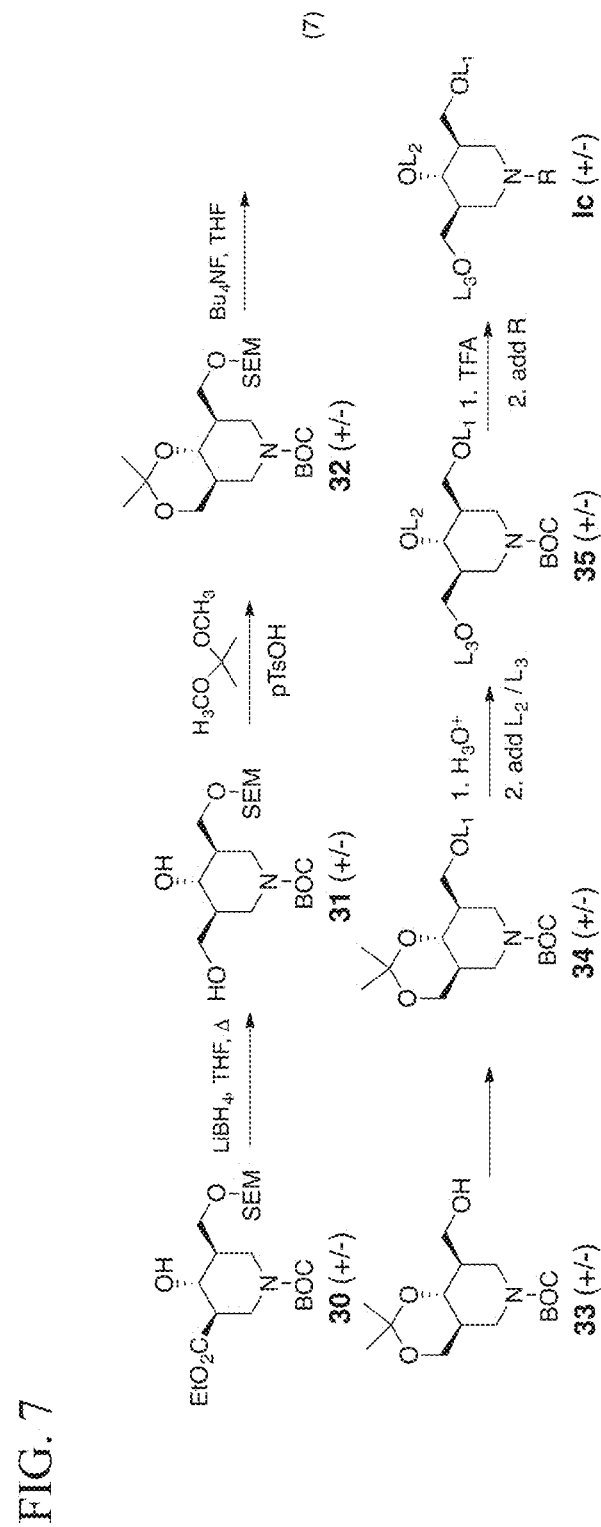
FIG. 7 shows equation (7) for the synthesis of the aminotriol of formula Ic.

The aminotriol of formula Ic is synthesized according to the method of equation (7) as shown in FIG. 7. The starting material of equation (7), compound 30, is prepared as described in Example 4 using the methods of Lohse.

Example 7

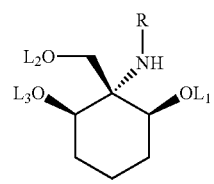

IIa

Figure 13:
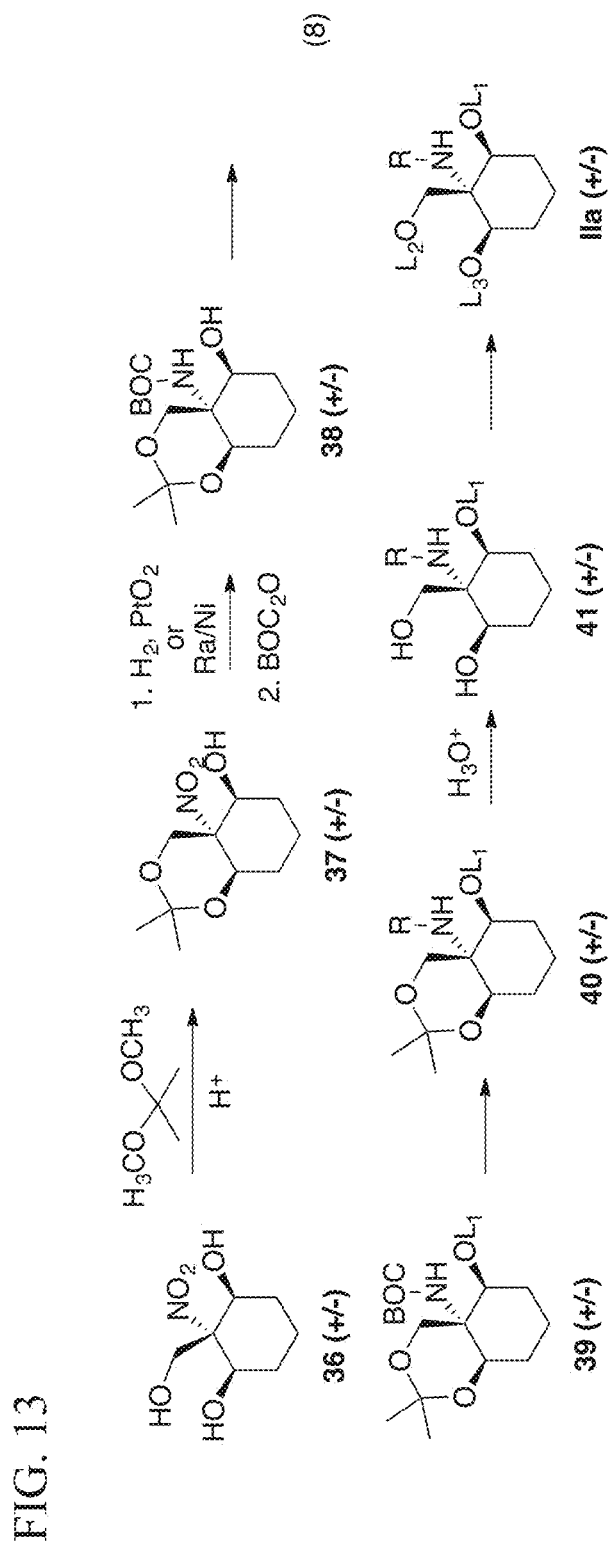
FIG. 13 shows equation (8) for the synthesis of the aminotriol of formula IIa.

The compound of formula IIa is synthesized according to the method shown in equation (8) of FIG. 13. The starting material of equation (8), compound 36, is prepared as described in Lichtenthaler, 1968, *Chem Ber*, 101:1815-18 and Zen, 1969, *Bull Chem Soc Japan*, 42:1761-62, hereby incorporated by reference, by cyclization of glutaraldehyde ($CHO(CH_2)_3CHO$) with nitroethanol ($OH(CH_2)_2)NO_2$) under nonaqueous conditions.

Example 8

An alteration in the standard GalNAc motif is used to exchange the standard 2-amino, 2-hydroxymethyl-1,3-propanediol motif for more rigid, stereochemically and sterically defined aminotriol replacements. Herein, a tethered cholesterol fragment is included as an example of an aminotriol structure within the framework of description for the cell-specificity afforded by the steroid moiety.

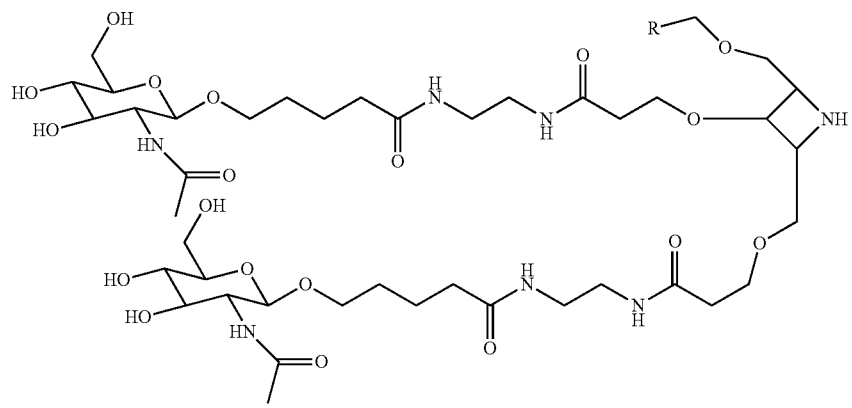

R = Cholesterol + various linkers

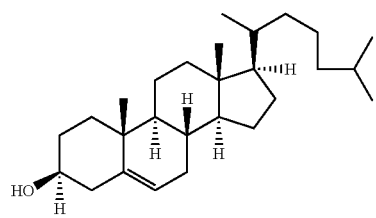

Compounds 1, 5, 9, 13, 19, and 30 of equations (1)-(7) afford either differentiated protecting functions with a single —OH moiety free for reaction, or the opportunity to manipulate protecting functions so as to allow a single —OH to be free for reaction. This provides the opportunity to selectively introduce the $L_1$, $L_2$, and $L_3$ moieties shown in FIGS. 1-7.

Figure 14:
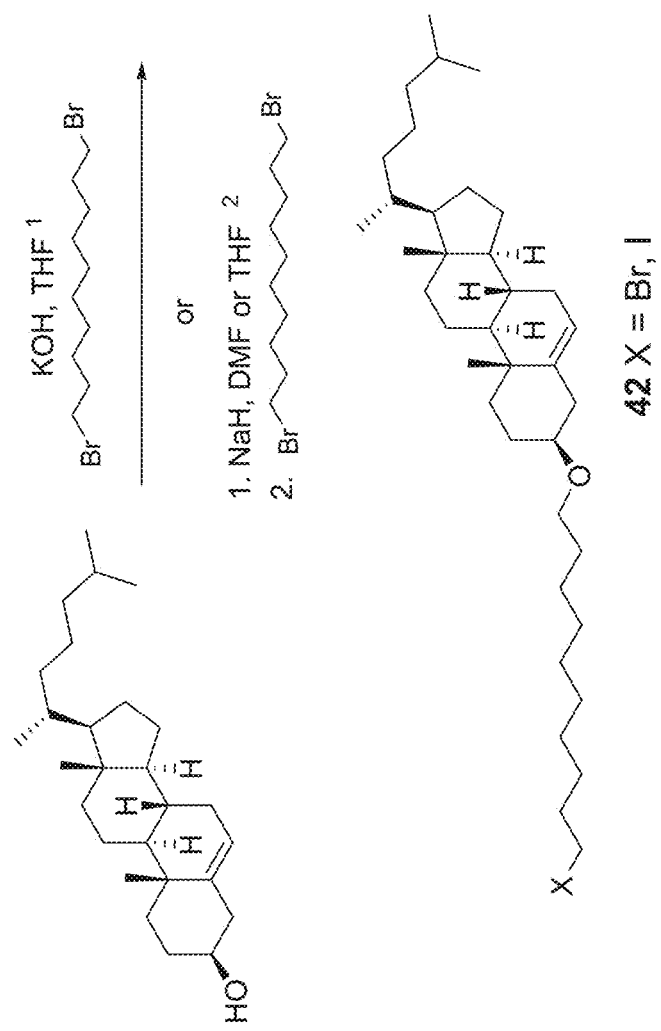
FIG. 14 shows preparation of the cholesterol-linker fragment 42.

A chain length of 10 carbons was selected for the tether between the cholesterol moiety and the aminotriol based upon chain availability. This occurs readily because diols are very common and can be converted to bis-electrophilic species quite readily. The cholesterol-tether moiety 42 is produced by the process shown in FIG. 14, using the methods of Wang, 2013, *Chemistry Asian J*, 8:101-07 and Wang, 2012, *J Mater Chem*, 22:7529-36, hereby incorporated by reference, to react cholesterol with $BrCH_2(CH_2)_8 CH_2Br$ in KOH/THF, or by the method of Wang, 2011, *Steroids*, 76:204-09 and Jensen, 2012, *J Liposome Res*, 22:295-305, hereby incorporated by reference, using NaOH/DMF or THF.

Example 9

Figure 15:
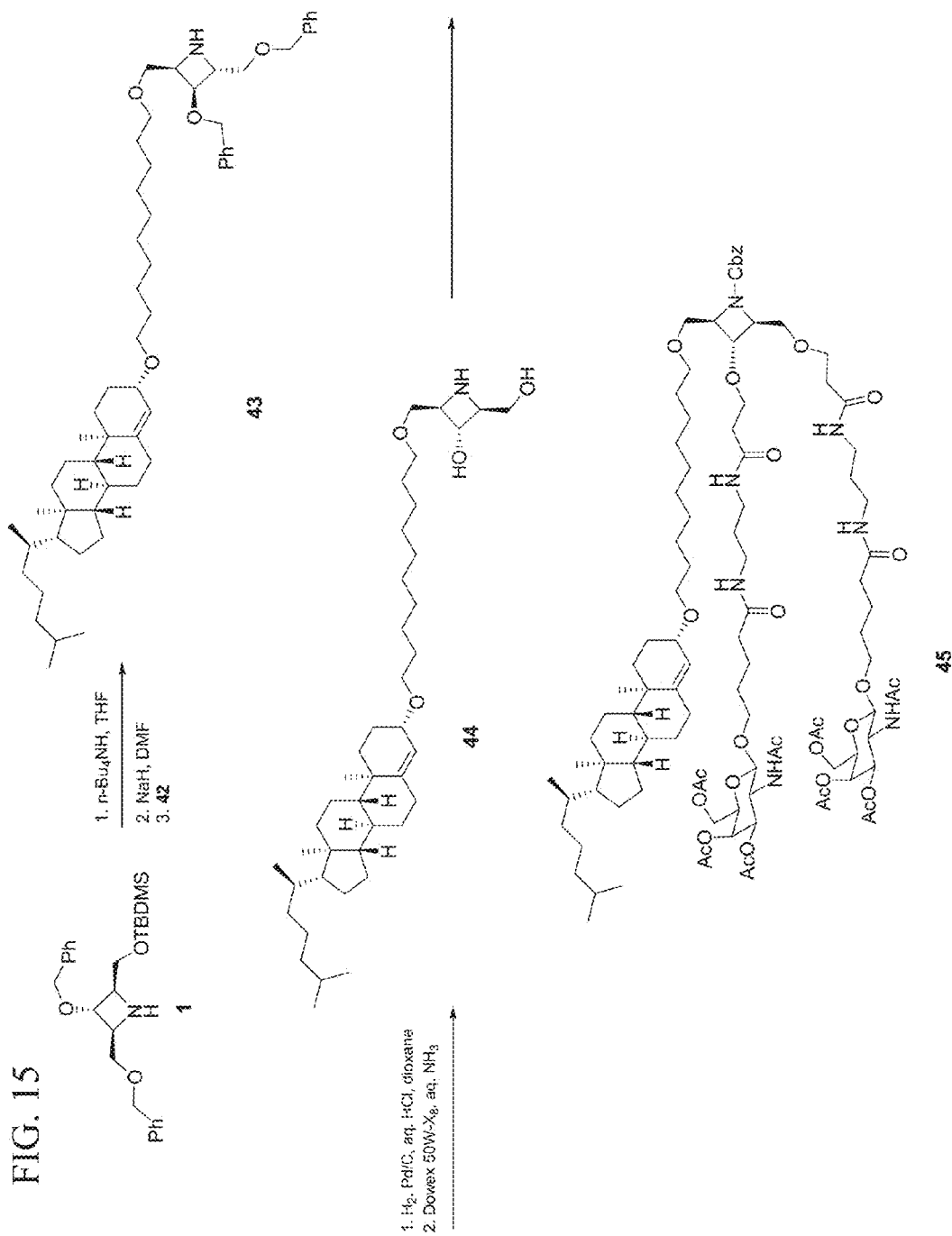
FIG. 15: shows the synthesis of azetidine-based/cholesterol conjugate 45.

The syntheses of the steroid modified/altered aminotriol GalNAc congeners are amenable to single points of reactivity as described above and here shown in the compound synthesized according to the reactions shown in FIG. 15. Starting with the differentially protected azetidine aminotriol 1, silyl cleavage (nBu$_4$NF) followed by introduction of the cholesterol-linker fragment 42 (NaH, THF or DMF) gives 43. Benzyl ether cleavage (as seen above in the preparation of the aminotriols: hydrogen Pd/C) exposes the previously blocked primary and secondary-OH groups (44) which allows the preparation of 45 after applying the chemistry outlined in FIG. 23.

Figure 16:
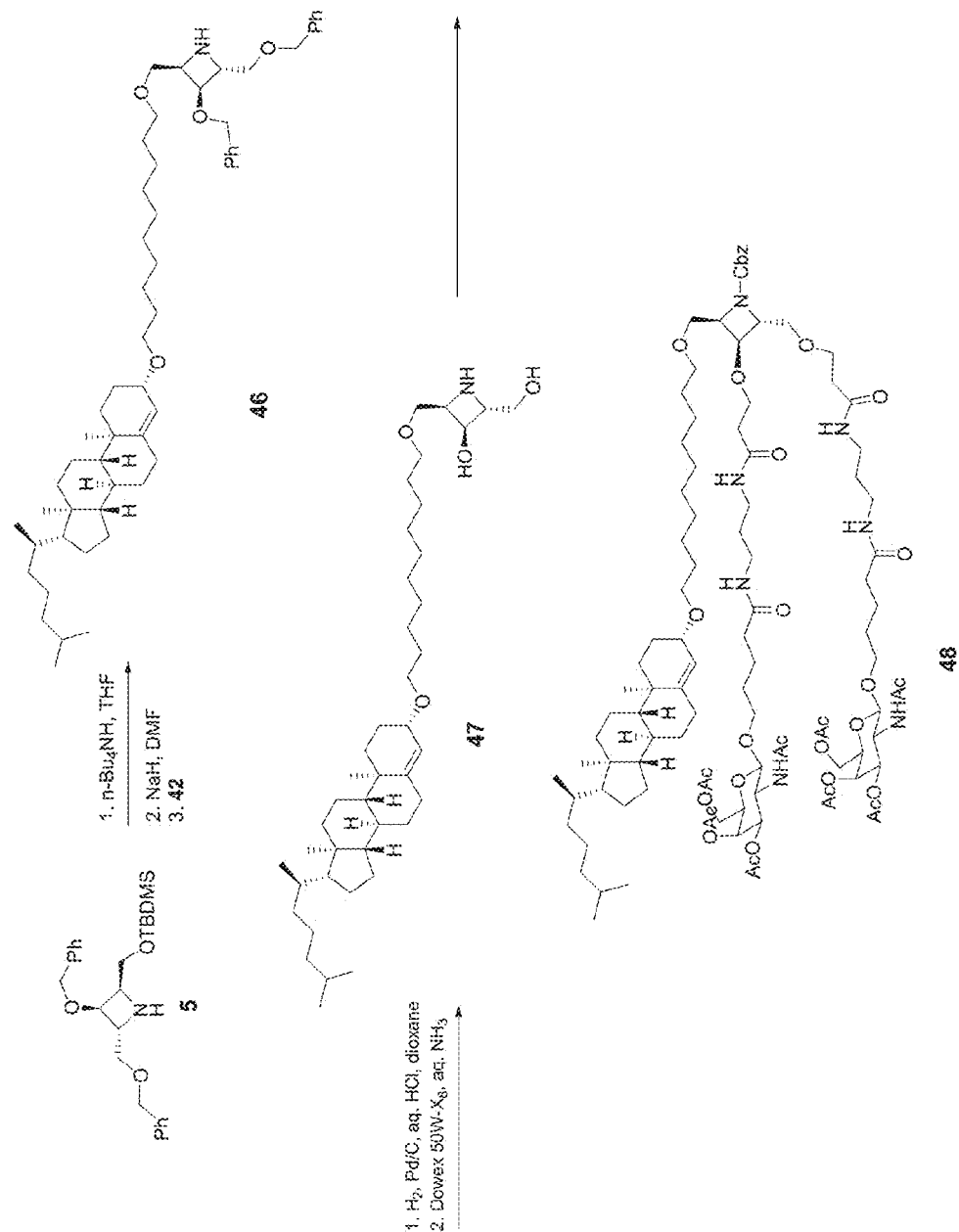
FIG. 16 shows the synthesis of azetidine-based/cholesterol conjugate 48.
Figure 17:
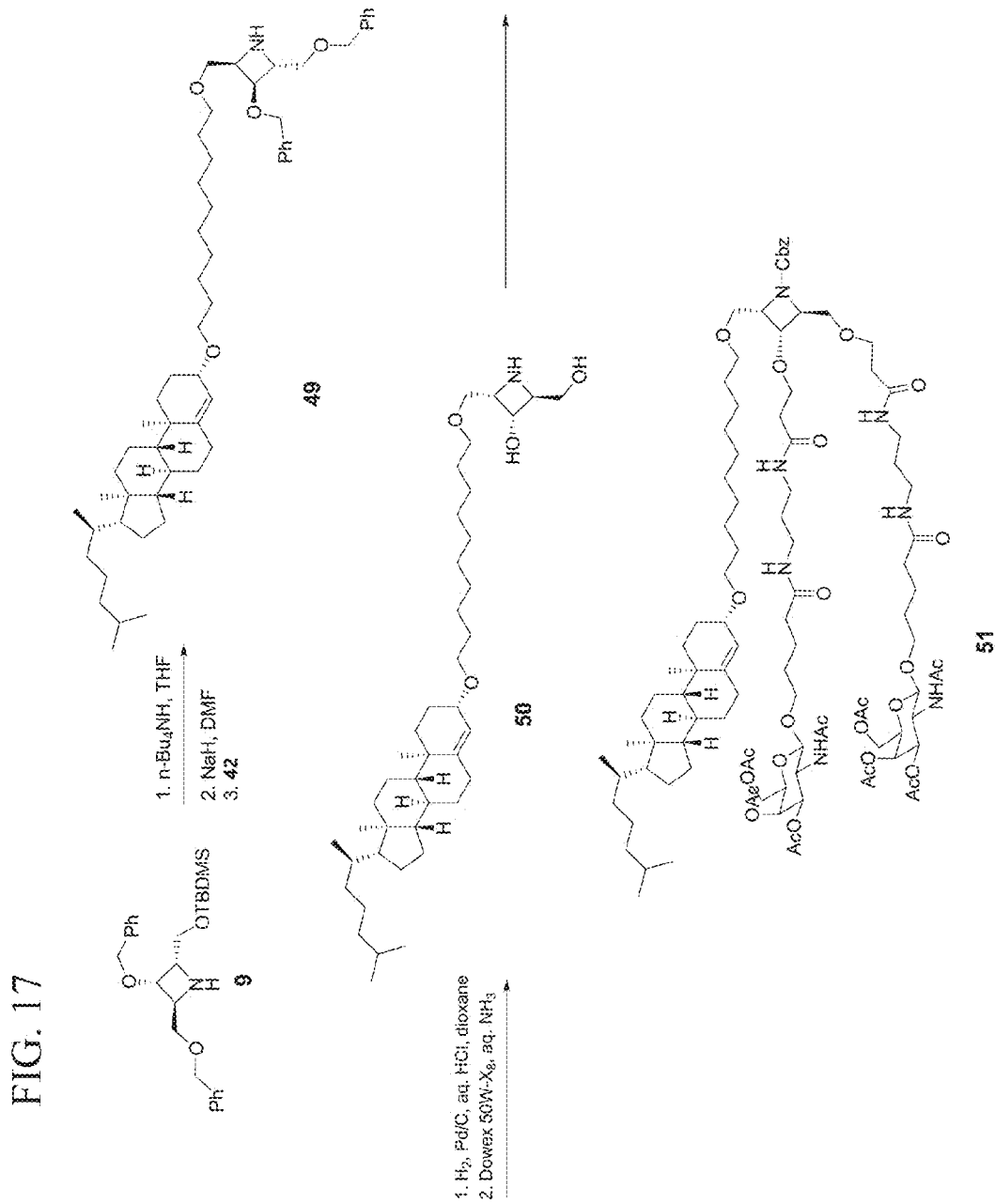
FIG. 17 shows the synthesis of azetidine-based/cholesterol conjugate 51.
Figure 18:
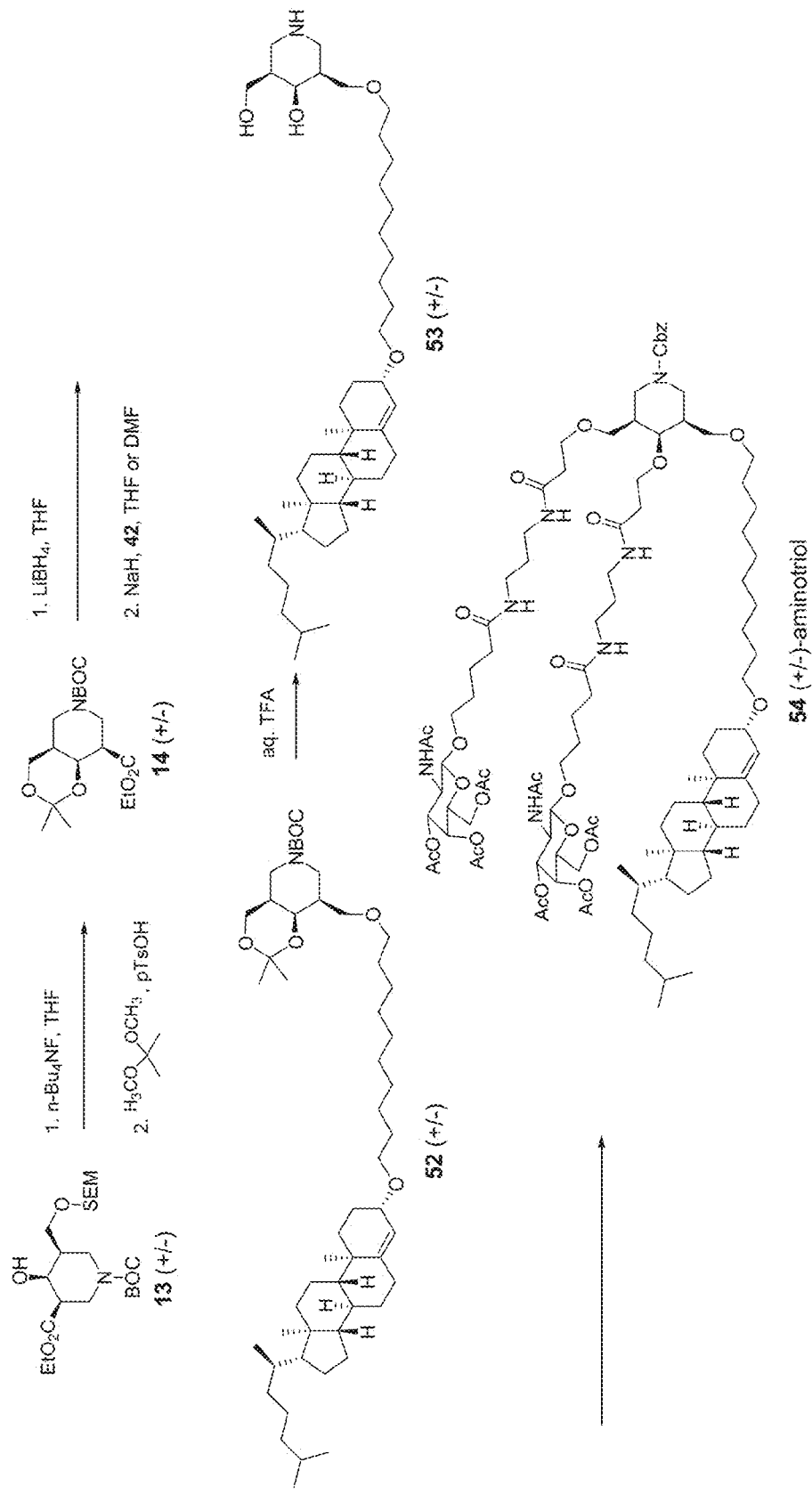
FIG. 18 shows the synthesis of piperidine based/cholesterol conjugate 54.
Figure 19:
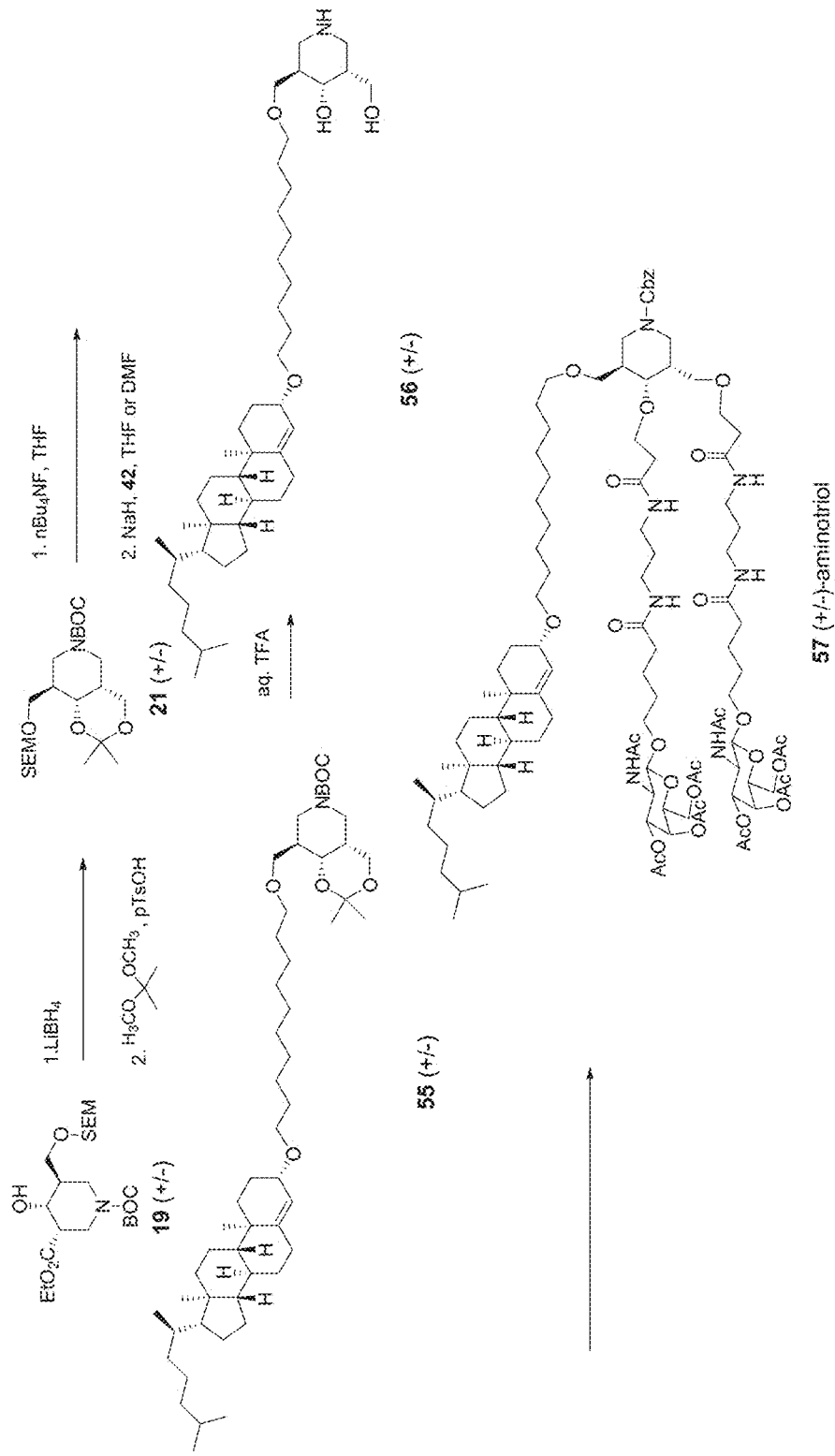
FIG. 19 shows the synthesis of piperidine based/cholesterol conjugate 57.
Figure 20:
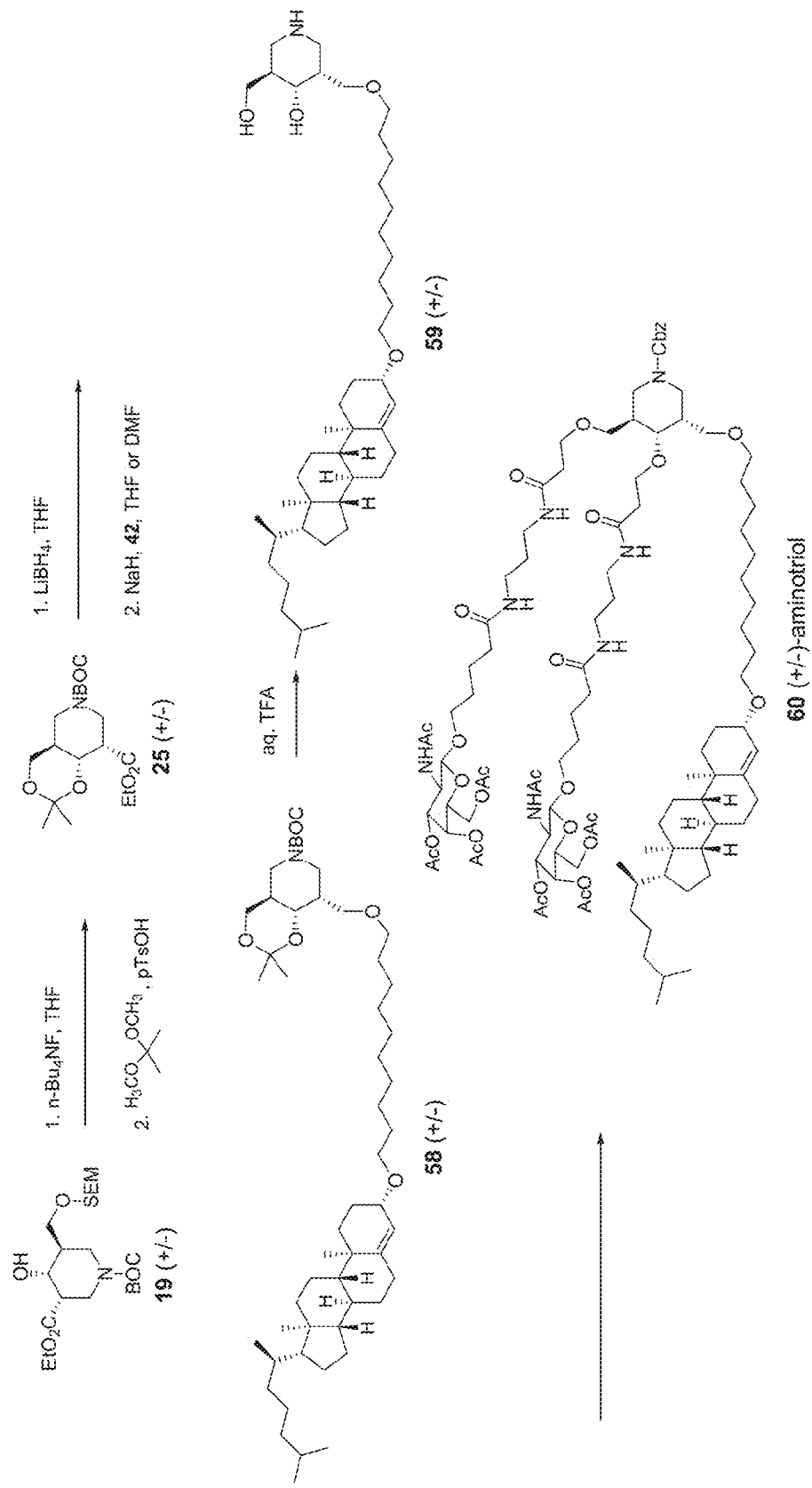
FIG. 20 shows the synthesis of piperidine based/cholesterol conjugate 60.
Figure 21:
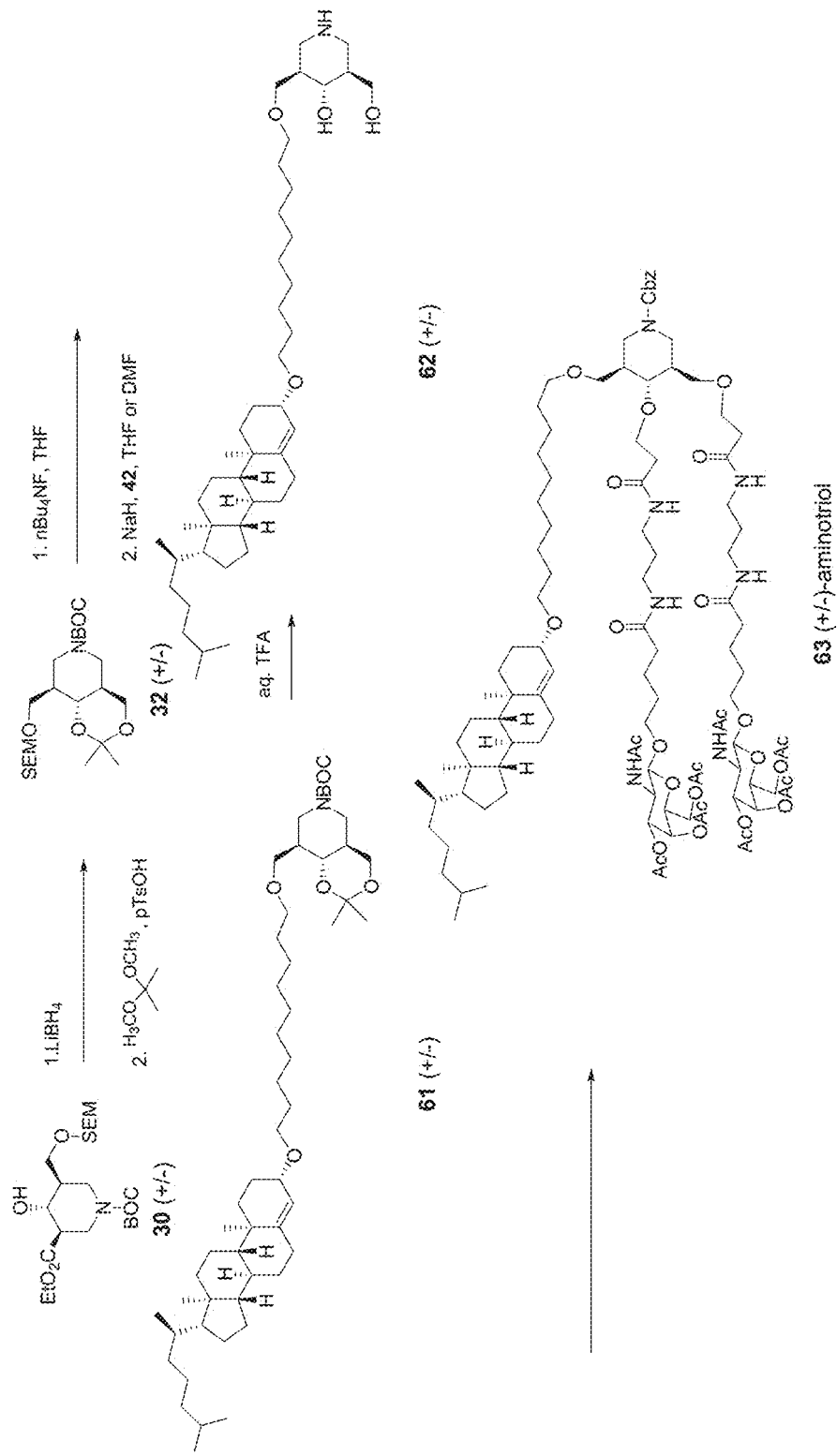
FIG. 21 shows the synthesis of piperidine based/cholesterol conjugate 63.

Similarly azetidine based, triprotected aminotriols 5 (FIG. 16) and 9 (FIG. 17) are reacted to give the steroid-conjugate GalNAc analogs 48 (FIG. 16) and 51 (FIG. 17).

Example 10

Figure 23:
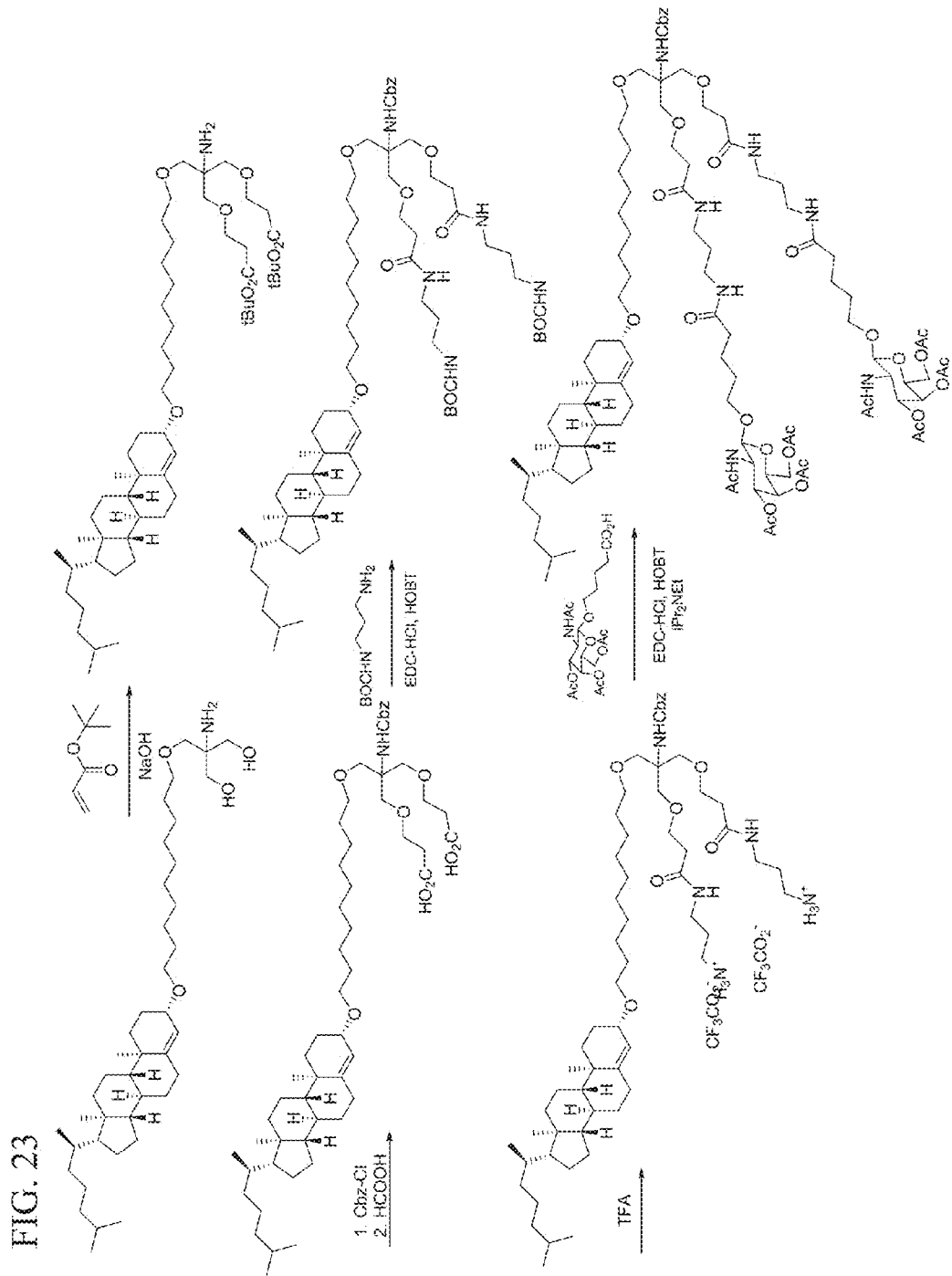
FIG. 23 shows the remaining steps utilized for the conversion of the initial cholesterol adduct to conjugates 45, 48, 51, 54, 57, 60, 63, and 66 referred to in FIGS. 15-22.

The syntheses of the piperidine based/cholesterol conjugates are shown in FIGS. 18, 19, 20 and 21. The mono-protected diol 13 (FIG. 18) is de-blocked (nBu$_4$NF) and the diol protected as the corresponding acetonide to afford 14. Reduction of the ester (LiBH$_4$) provides an alcohol which can be alkylated with 42 to provide 52. The ketal and the BOC group are removed with aqueous TFA to yield 53 which leads to the desired 54 after application of the chemistry described in FIG. 23. Compound 19 (FIG. 19) is reduced and ketalized to give 21, which leads to the construction of 57. An alternate regiochemistry is realized from 19 (FIG. 20) when 19 is first deprotected with nBu$_4$NF to give 25 after protection as an acetonide. Deprotection of the SEM ether (nBu$_4$NF) provides an alcohol which would give 58 after alkylation with 42. The ketal and the BOC group are removed with aqueous TFA to yield 59 which leads to the desired 60 (FIG. 20) after application of the chemistry described in FIG. 23. The mono-protected piperidine-diol 30 (FIG. 21) is reduced and the diol protected as an acetonide to give 32. SEM-deprotection and alkylation with 42 gives 61. Treatment with aqueous TFA cleaves the ketal and the BOC group to afford 62 which, after the application of the chemistry of FIG. 23, gives the desired 63.

Example 11

Figure 22:
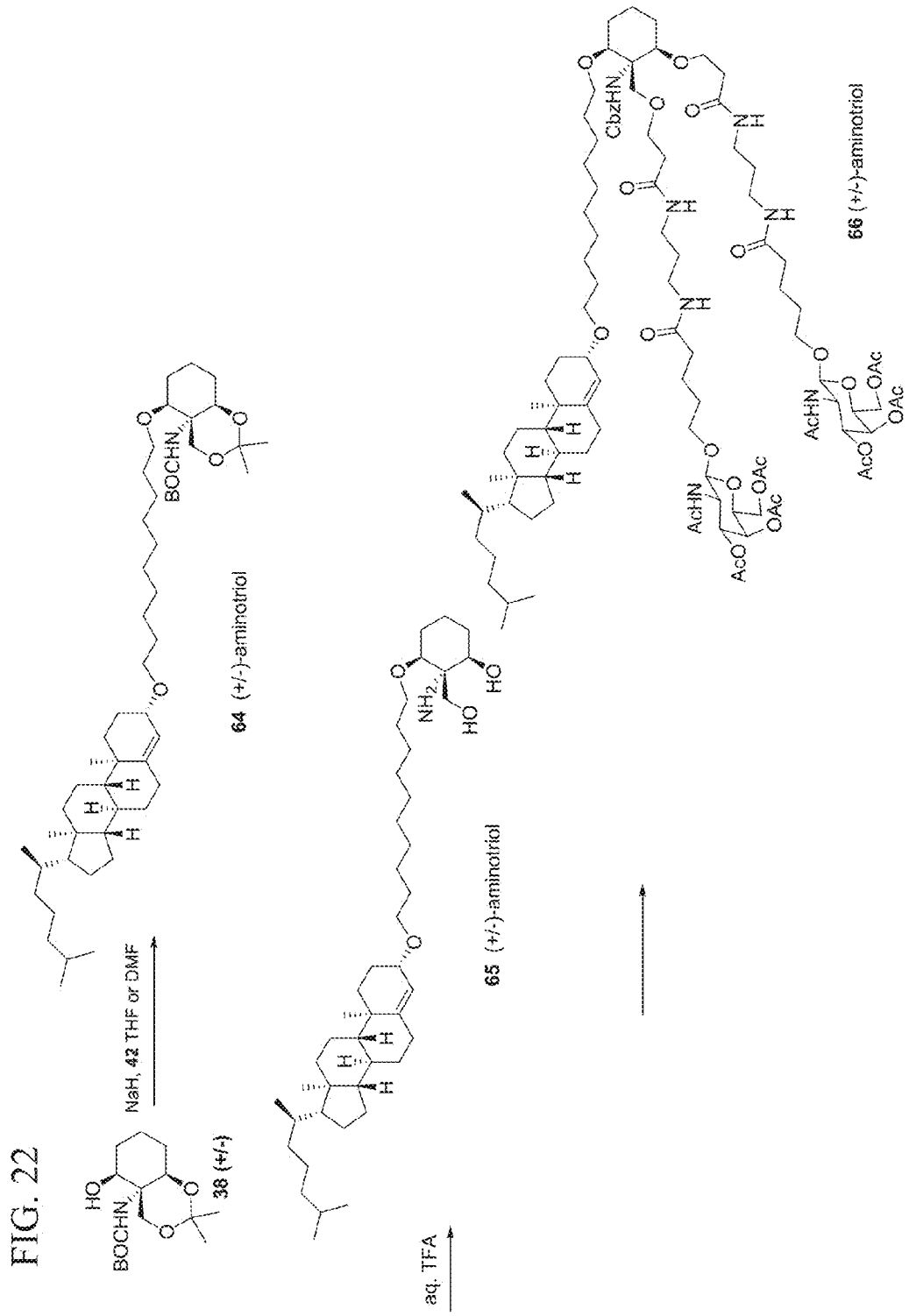
FIG. 22 shows the synthesis of cyclohexane based/cholesterol conjugate 66.

The synthesis of a cyclohexane-based cholesterol conjugate is shown in FIG. 22. Acetonide 38 is alkylated with 42 to give 64. The ketal and the BOC group are removed with aqueous TFA to yield 65 which leads to the desired 66 after application of the chemistry described in FIG. 23.

Example 12

Figure 24A:
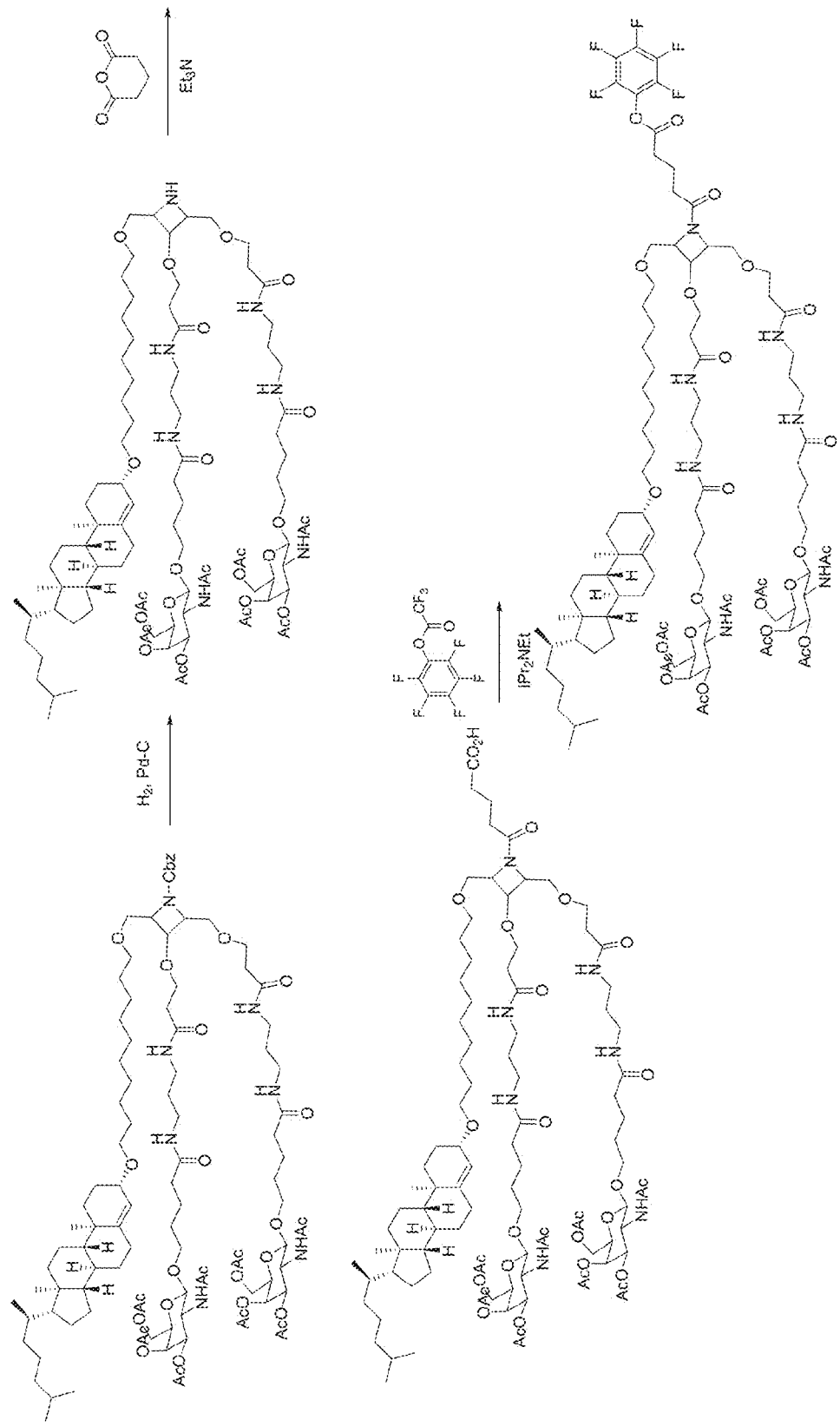
FIG. 24A shows the solution phase synthesis introducing RNA to an azetadine-based/cholesterol conjugate of FIGS. 15-17.
Figure 24B:
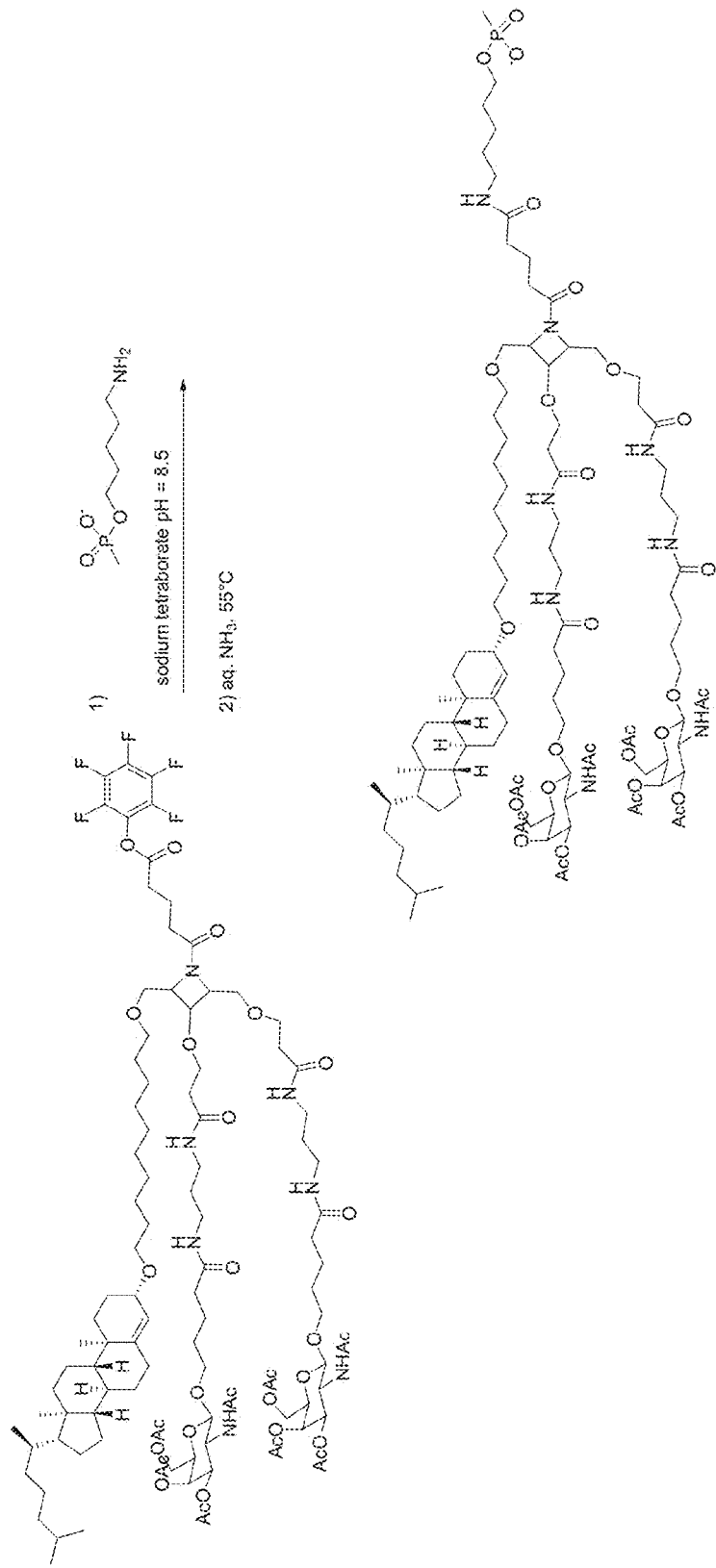
FIG. 24B continues the solution phase synthesis shown in FIG. 24A.

A solution phase synthesis introducing RNA to the aminotriol conjugates is shown in FIG. 24A and FIG. 24B. The amino-protecting group is removed by hydrogen and palladium. The resulting amino group is reacted with glutaric anhydride and triethylamine to produce an amide linkage and a free carboxyl. This product is reacted with perfluorophenyl 2,2,2-trifluroroacetate to produce an ester with a pentafluorophenyl leaving group. This product is reacted with 5-aminopentyl methylphosphonate to produce a aminotriol conjugate with a free phosphate group for ligation with a nucleic acid.

Figure 25A:
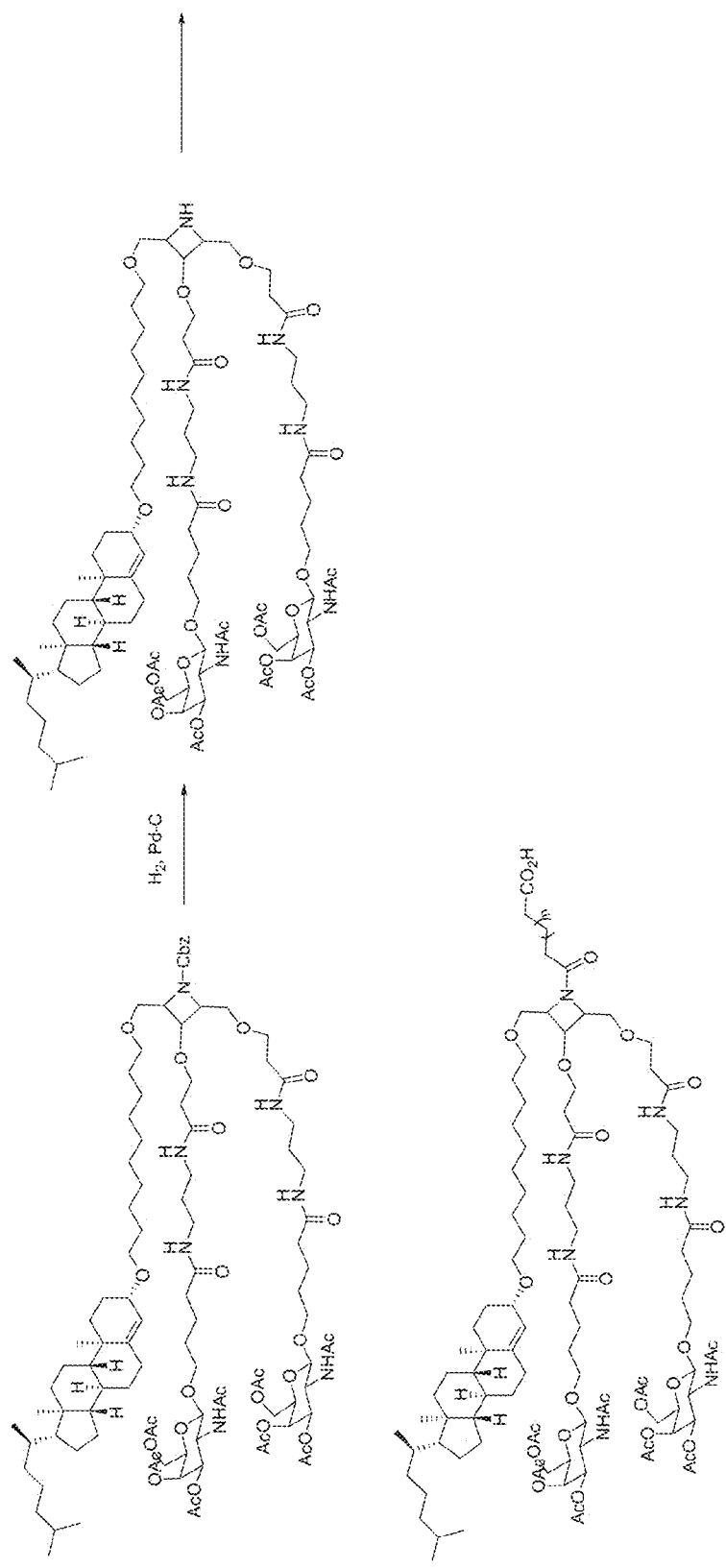
FIG. 25A shows the solid phase synthesis introducing RNA to an azetadine-based/cholesterol conjugate of FIGS. 15-17.
Figure 25B:
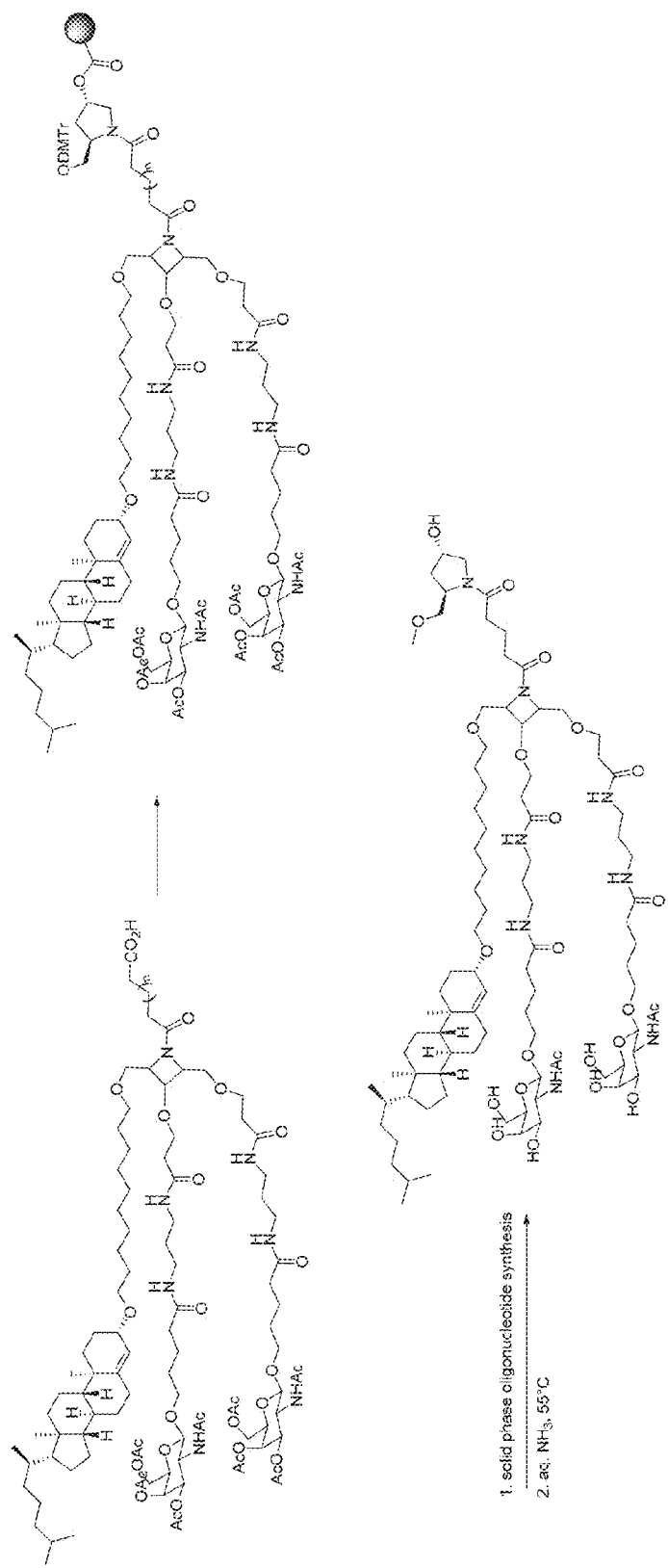
FIG. 25B continues the solid phase synthesis shown in FIG. 25A.

A solid phase synthesis introducing RNA to the aminotriol conjugates is shown in FIG. 25A and FIG. 25B. The amino-protecting group is removed by H2 and palladium. The resulting amino group is reacted with glutaric anhydride and triethylamine to produce an amide linkage and a free carboxyl. This product is prepared for reaction with a solid phase nucleic acid synthesizer.

The disclosures of all publications cited herein are hereby incorporated by reference into the present description.

What is claimed:

1. A compound consisting of an aminotriol of formula I, II, or III,

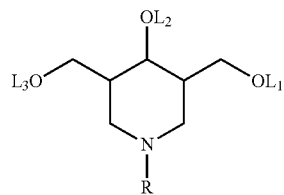

I

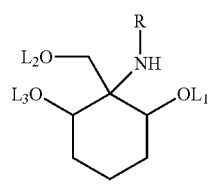

II

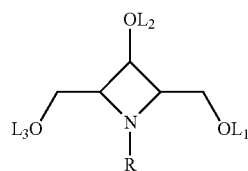

III wherein R comprises a biologically active molecule, and $L_1$, $L_2$, and $L_3$ independently for each occurrence comprise a ligand selected from the group consisting of a carbohydrate, a polypeptide, or a lipophile; a pharmaceutically acceptable salt thereof; or a pharmaceutical composition thereof.

2. The compound claim 1, having the structure of formula Ia, 1b, or 1c

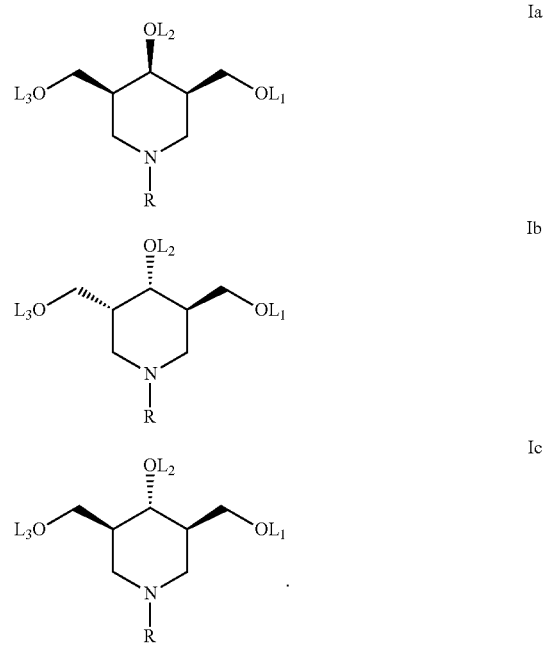

3. The compound of claim 1, having the structure of formula IIa

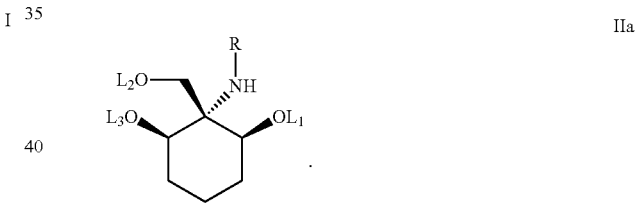

4. The compound of claim 1, having the structure of formula IIIa, IIIb, or IIIc

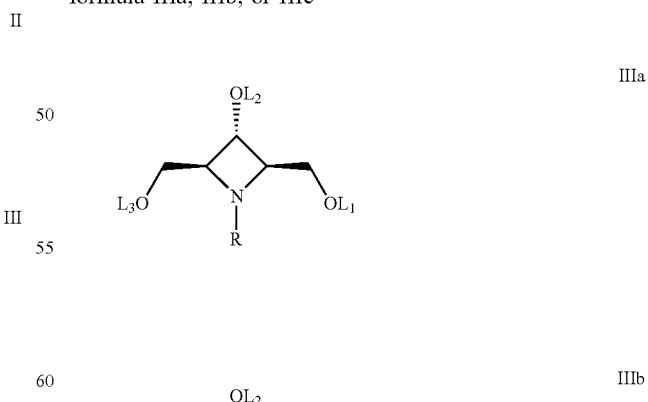

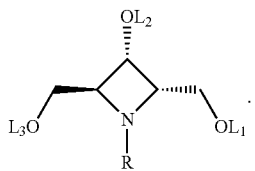

IIIc

5. The compound of claim 1, wherein the biologically active molecule is a therapeutic molecule selected from an antibody, a polynucleotide, a hormone, an antibiotic, or a drug having a molecular weight less than 1,000 Daltons.

6. The compound of claim 5, wherein the biologically active molecule is a RNA molecule, comprising a sense and an antisense strand.

7. The compound of claim 6, wherein the aminotriol is covalently attached at the 3'-end of the sense strand, the 5'-end of the sense strand, the 3'-end of the antisense strand, or the 5'-end of the antisense strand.

8. The compound of claim 7, wherein R further comprises a phosphate moiety having the structure —O—P(Z')(Z")-O—, wherein Z' and Z" are independently for each occurrence O or S, and wherein the phosphate moiety is covalently attached to a 3'-end or 5'-end of the RNA molecule.

9. The compound of claim 1, wherein one or more of R, $L_1$, $L_2$, or $L_3$ further comprises a linker comprising the structure -(A-B$^1$-Z)$_n$-D$^1$- or

-D$^1$-B$^1$-D$^{1'}$-E-D$^{2'}$—B$^2$-D$^2$- wherein

A, D$^1$, D$^{1'}$, D$^2$, D$^{2'}$ are independently for each occurrence absent, CO, NH, O, S, OC(O), NHC(O), CH$_2$, CH$_2$NH, or CH$_2$O;

B$^1$ and B$^2$ are for each occurrence absent, alkylene, substituted alkylene wherein one or more methylenes can be interrupted or terminated by one or more of O, S, S(O), SO$_2$, N(R$^N$), C(R')=C(R"), or C(O), wherein R' and R" are each independently H, C$_1$-C$_6$ alkyl, OH, SH, or N(R$^N$)$_2$, and R$^N$ is for each occurrence independently methyl, ethyl, propyl, isopropyl, butyl, or benzyl;

Z is absent, NH, O, S, CH$_2$, C(O)O, C(O)NH, NHCH(R$^a$)C(O), C(O)CH(R$^a$)NH, CO, CH=NO, or heterocyclyl, wherein R$^a$ is H or an amino acid side chain;

E is —CH$_2$N(E$^L$)CH$_2$—, wherein E$^L$ is -D$^3$-B$^3$-D$^{3'}$-R$^x$, wherein D$^3$ and D$^{3'}$ are each independently for each occurrence absent, CO, NH, O, S, OC(O), OC(O)O, NHC(O), NHC(O)NH, NHC(O)O, CH$_2$, CH$_2$NH, or CH$_2$O, and R$^x$ is a cholesteryl or a cationic lipid; and n is 0, 1, 2, 3, 4, 5, 6, 7, 8, 9, 10, 11, 12, 13, 14, 15, 16, 17, 18, 19, or 20.

10. The compound of claim 1, wherein one or more $L_1$, $L_2$, and $L_3$ comprise a lipophile selected from cholesteryl, cholic acid, adamantane acetic acid, 1-pyrene butyric acid, dihydrotestosterone, 1,3-bis-O(hexadecyl)glycerol, geranyloxyhexyl, hexadecylglycerol, borneol, menthol, 1,3-propanediol, heptadecyl, palmitic acid, myristic acid, O-3-(oleoyl)lithocholic acid, O-3-(oleoyl)cholenic acid, dimethoxytrityl, and phenoxazine.

11. The compound of claim 1, wherein one or more of $L_1$, $L_2$, and $L_3$ comprise a carbohydrate, wherein the carbohydrate is a monosaccharide selected from, N-acetyl-galactosamine (GalNAc), allose, altrose, arabinose, cladinose, erythrose, erythrulose, fructose, D-fucitol, L-fucitol, fucosamine, fucose, fuculose, galactosamine, D-galactosaminitol, galactose, glucosamine, N-acetyl-glucosamine, glucosaminitol, glucose, glucose-6-phosphate, gulose glyceraldehyde, L-glycero-D-mannos-heptose, glycerol, glycerone, gulose, idose, lyxose, mannosamine, mannose, mannose-6-phosphate, psicose, quinovose, quinovosamine, rhamnitol, rhamnosamine, rhamnose, ribose, ribulose, sedoheptulose, sorbose, tagatose, talose, tartaric acid, threose, xylose and xylulose.

12. The compound of claim 11, wherein the carbohydrate is GalNAc, or galactose.

13. The compound of claim 1, wherein and $L_1$, $L_2$, and/or $L_3$ comprise a polypeptide ligand for a cellular receptor.

14. A process of making a multiligand compound shown formula 45

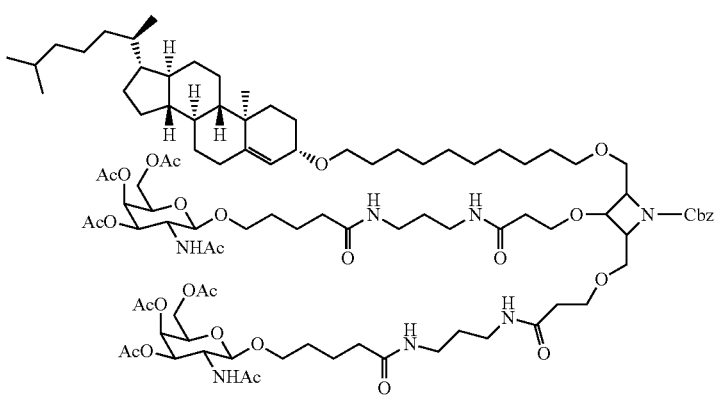

45 the process comprising the steps of
i. reacting aminotriol compound

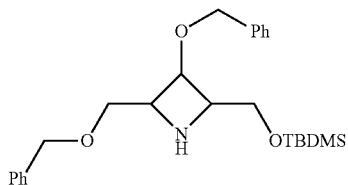

with a lipophile 42,

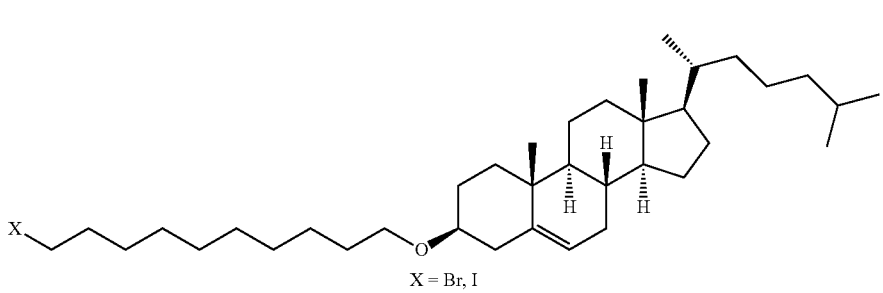

X = Br, I ii. removing hydroxyl protecting groups from the product of step i;
iii. reacting the product of step ii with (CHCH)COO-t-butyl in NaOH;
iv. adding an amino protecting group to the product of step iii;
v. reacting the product of step iv with BocN(CH$_2$)$_3$NH$_2$ using 1-ethyl-3-(3-dimethylaminopropyl)carbodiimide-hydrochloride (EDC) and hydroxybenzotriazole (HOBT);
vi. reacting the product of step v with GalNAc acid using EDC, HOBT, and N,N-diisopropylethylamine.

15. The process of claim 14, wherein the aminotriol compound is 1, 5, or 9

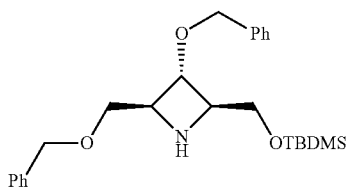

-continued

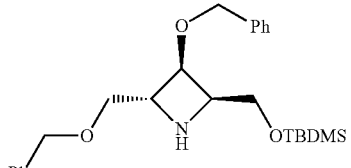

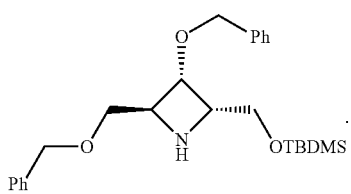

16. A process of making a multiligand compound shown formula 53

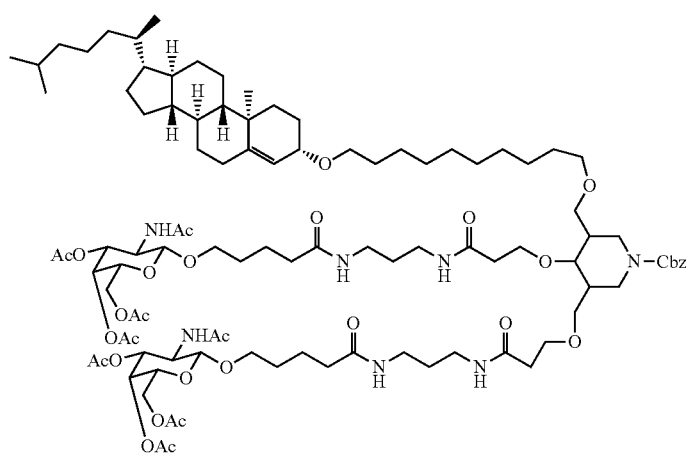

the process comprising the steps of
i. reacting aminotriol compound

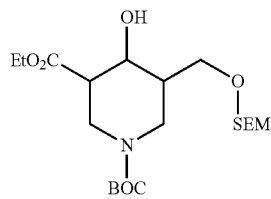 [SMILES: CCOC(=O)C1CN(C(=O)OC(C)(C)C)CC(COCOCC[Si](C)(C)C)C1O]

with n-Bu4NF,
ii. reacting the product of step i with CH$_3$C(OCH$_3$)$_2$CH$_3$ and p-toluenesulfonic acid,
iii. reacting the product of step ii with LiBH$_4$,
iv. reacting the product of step iii with a lipophile 42,
v. removing hydroxyl protecting groups from the product of step iv;
vi. reacting the product of step v with (CHCH)COO-t-butyl in NaOH;
vii. adding an amino protecting group to the product of vi;
viii. reacting the product of step viii with BocN(CH$_2$)$_3$NH$_2$ using 1-ethyl-3-(3-dimethylaminopropyl)carbodiimide-hydrochloride (EDC) and hydroxybenzotriazole (HOBT);
ix. reacting the product of step viii with GalNAc acid

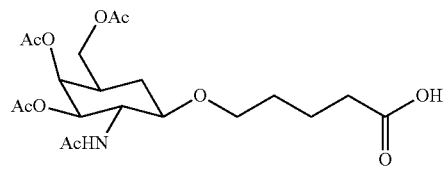 [SMILES: CC(=O)NC1C(OCCCCC(=O)O)CC(COC(C)=O)C(OC(C)=O)C1OC(C)=O]

using EDC, HOBT, and N,N-diisopropylethylamine.

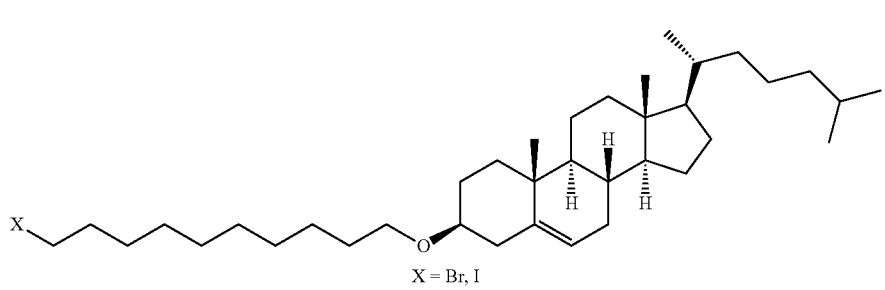

X = Br, I

17. The process of claim 16, wherein the aminotriol compound is 13, 19, or 30

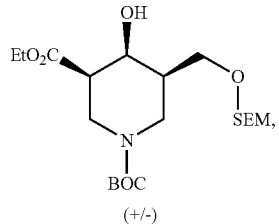

13

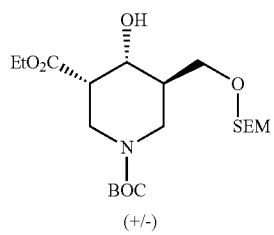

19

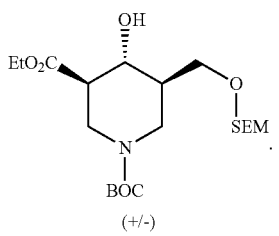

30

18. A method of treating a disease comprising administering a therapeutically effective amount of a pharmaceutical composition comprising the compound of claim 1, wherein the therapeutic molecule is an RNA molecule.

19. The method of claim 18, where the pharmaceutical composition is administered subcutaneously.

* * * * *